United States Patent [19]

Fontayne et al.

[11] Patent Number: 5,454,824
[45] Date of Patent: Oct. 3, 1995

[54] FRAGMENTABLE RING APPLIER

[75] Inventors: Diego Fontayne, Norwalk; John C. Robertson, Bloomfield; Timothy O. Van Leeuwen, Brookfield; Thomas A. Pelletier, Wallingford; Stephen W. Gerry, Bethel, all of Conn.

[73] Assignee: United States Surgical Corporation, Norwalk, Conn.

[21] Appl. No.: 125,382

[22] Filed: Sep. 22, 1993

Related U.S. Application Data

[63] Continuation-in-part of Ser. No. 959,152, Oct. 9, 1992, Pat. No. 5,376,098.

[51] Int. Cl.$^6$ .................................................. A61B 17/00
[52] U.S. Cl. .................................... 606/151; 606/154
[58] Field of Search ................................ 606/151, 153, 606/154, 142, 143, 213, 215; 227/175–181, 19, 901; 128/4

[56] References Cited

U.S. PATENT DOCUMENTS

| | | |
|---|---|---|
| D. 271,994 | 12/1983 | Noiles et al. |
| D. 273,041 | 3/1984 | Noiles et al. |
| 606,511 | 6/1898 | Buckles. |
| 3,193,165 | 7/1965 | Akhalaya et al. |
| 3,552,626 | 1/1971 | Astafiev et al. |
| 3,557,780 | 1/1971 | Sato ............................................ 128/4 |
| 3,593,903 | 7/1971 | Astefiev et al. |

(List continued on next page.)

FOREIGN PATENT DOCUMENTS

| | | |
|---|---|---|
| 1136020 | 11/1982 | Canada. |
| 0152382 | 8/1985 | European Pat. Off. |
| 0503689 | 9/1992 | European Pat. Off. |
| 0517488 | 12/1992 | European Pat. Off. |
| 0540010 | 5/1993 | European Pat. Off. .............. 227/19 |
| 7930018 | 12/1979 | France. |
| 3301713 | 11/1989 | Germany. |
| 1509052 | 9/1989 | U.S.S.R. |

| | | |
|---|---|---|
| WO89/00406 | 1/1989 | WIPO. |
| WO90/05489 | 5/1990 | WIPO. |
| WO90/06085 | 6/1990 | WIPO. |

OTHER PUBLICATIONS

Article entitled "Clinical Application of a New Compression Anastomotic Device for Colorectal Surgery" by Carlo Rebuffat, M.D. et al. published in the American Journal of Surgery, vol. 159, pp. 330–335, Mar. 1990.

Article entitled "A New Mechanical Device for Circular Compression Anastomosis" by R. Rosati M.D., et al. presented at the First Surgical Clinic–University of Milan, Italy, Ann–Surg., pp. 245–252, Mar. 1988.

"Information Booklet for an Auto Suture, Surgical Stapling Instrument," United States Surgical Corporation, 1984.

*Primary Examiner*—Stephen C. Pellegrino
*Assistant Examiner*—Jeffrey A. Schmidt

[57] ABSTRACT

A novel surgical instrument suitable for insertion and assembly of surgical fasteners, such as multi-ring compression devices, for circular anastomosis of tubular or hollow organ tissue sections, including a body having means to support and align the rings, means for clamping the rings around the free ends of the tissue sections, means for coring away excess clamped tissue and the centers of the rings, separate means for releasing the clamped rings from the instrument and dwell means to delay releasing the rings until after the coring operation is complete. The dwell means consists of an external cup containing separate and coaxial elements for the coring means and the releasing means which are provided with a series of recesses and a plurality of shifter keys to separate the operation of coring from the separate operation of releasing the assembled multi-ring compression device from the instrument. The instrument may additionally include means for detaching a portion of the support means to facilitate installation and alignment, a safety to ensure safe operation and various knife blade profiles. Additionally, the surgical instrument may be provided with a longitudinal bore extending throughout the length of the instrument for receipt of accessory instruments therethrough. Further, lockout means may be provided to block the coring means until the rings have been clamped around the tissue sections.

10 Claims, 25 Drawing Sheets

U.S. PATENT DOCUMENTS

| | | |
|---|---|---|
| 3,765,282 | 10/1973 | Crain, Jr. . |
| 4,027,510 | 6/1977 | Hiltebrandt . |
| 4,207,898 | 6/1980 | Becht . |
| 4,277,891 | 7/1981 | Dick . |
| 4,304,236 | 12/1981 | Conta et al. . |
| 4,319,576 | 3/1982 | Rothfuss . |
| 4,351,466 | 9/1982 | Noiles . |
| 4,379,457 | 4/1983 | Gravener et al. . |
| 4,485,817 | 12/1984 | Swiggett . |
| 4,488,523 | 12/1984 | Shichman . |
| 4,493,319 | 1/1985 | Polk et al. . |
| 4,573,468 | 3/1986 | Conta et al. . |
| 4,576,167 | 3/1986 | Noiles . |
| 4,598,712 | 7/1986 | Rebuffat et al. . |
| 4,603,693 | 8/1986 | Conta et al. . |
| 4,606,343 | 8/1986 | Conta et al. . |
| 4,646,745 | 3/1987 | Noiles . |
| 4,667,673 | 5/1987 | Li . |
| 4,681,108 | 7/1987 | Rosati et al. . |
| 4,752,024 | 6/1988 | Green et al. . |
| 4,776,506 | 10/1988 | Green . |
| 4,817,847 | 4/1989 | Redtenbacher et al. . |
| 4,848,367 | 7/1989 | Avant et al. . |
| 4,873,977 | 10/1989 | Avant et al. . |
| 4,880,015 | 11/1989 | Nierman . |
| 4,893,622 | 1/1990 | Green et al. . |
| 4,907,591 | 3/1990 | Vasconcellos et al. . |
| 4,917,114 | 4/1990 | Green et al. . |
| 4,931,057 | 6/1990 | Cummings et al. . |
| 4,935,027 | 6/1990 | Yoon ................ 606/146 |
| 4,957,499 | 9/1990 | Lipatov et al. . |
| 4,964,863 | 10/1990 | Kanshin et al. . |
| 4,966,602 | 10/1990 | Rebuffat et al. . |
| 5,005,749 | 4/1991 | Aranyl . |
| 5,047,039 | 9/1991 | Avant et al. . |
| 5,119,983 | 6/1992 | Green et al. . |
| 5,122,156 | 6/1992 | Granger et al. . |
| 5,139,513 | 8/1992 | Segato . |
| 5,222,963 | 6/1993 | Brinkerhoff et al. ........ 227/179 |
| 5,257,618 | 11/1993 | Kondo ................ 128/4 |
| 5,290,299 | 3/1994 | Fain et al. ................ 606/142 |

FIG.14a
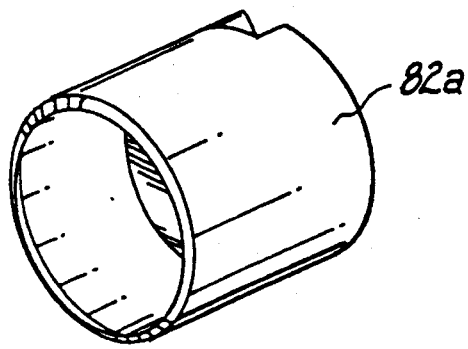
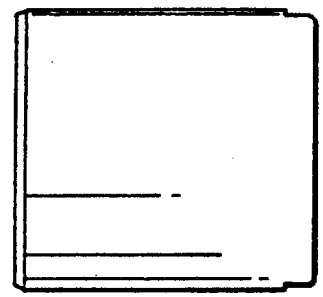
FIG.14aa
FIG.14c
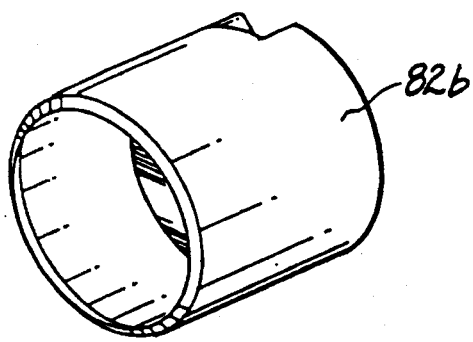
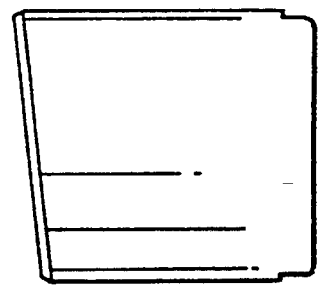
FIG.14cc
FIG.14b
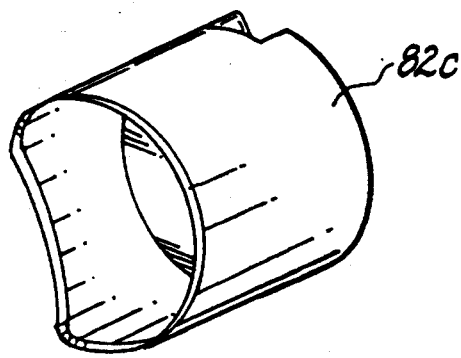
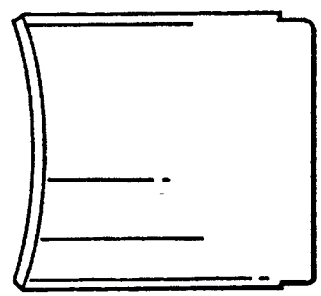
FIG.14bb

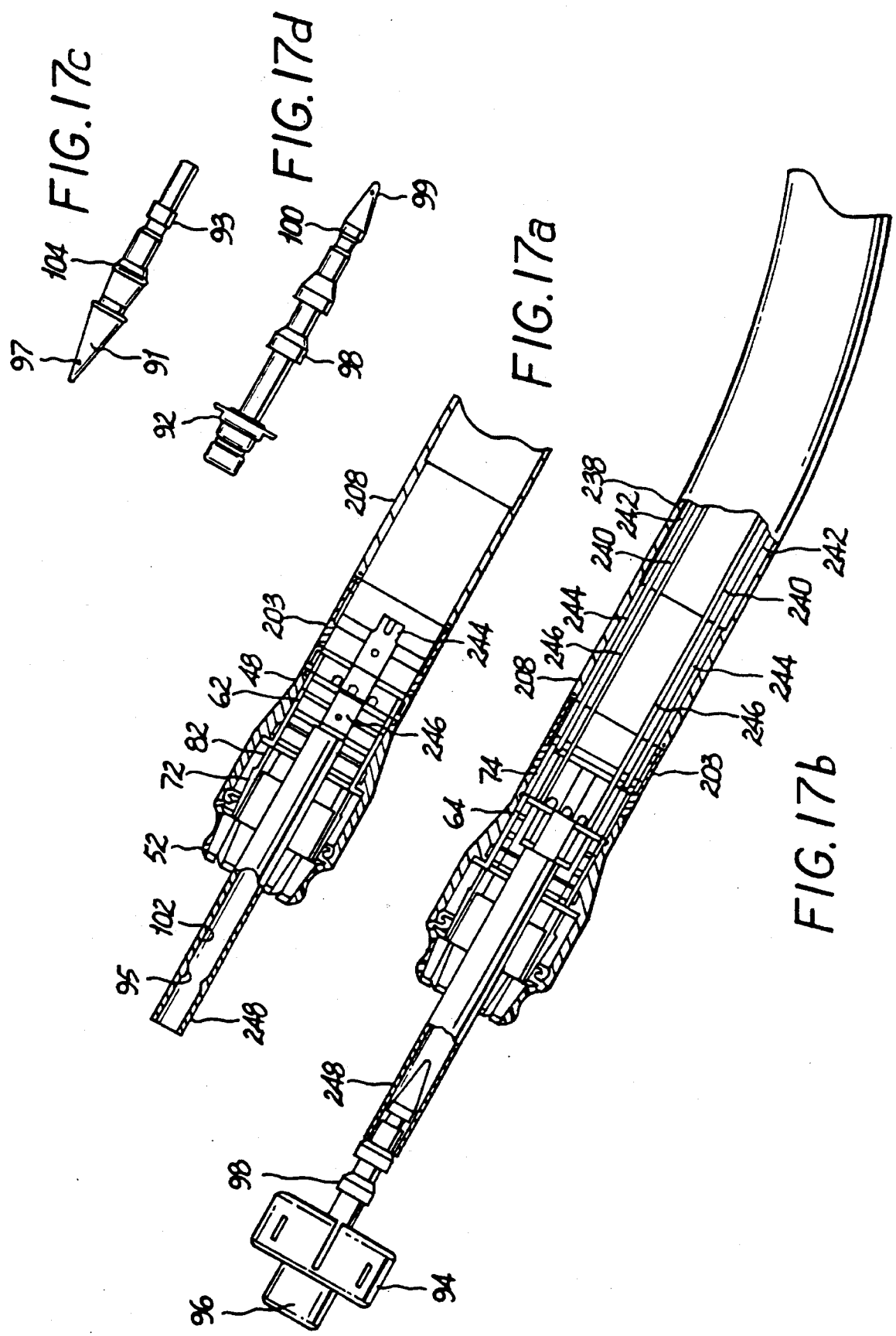

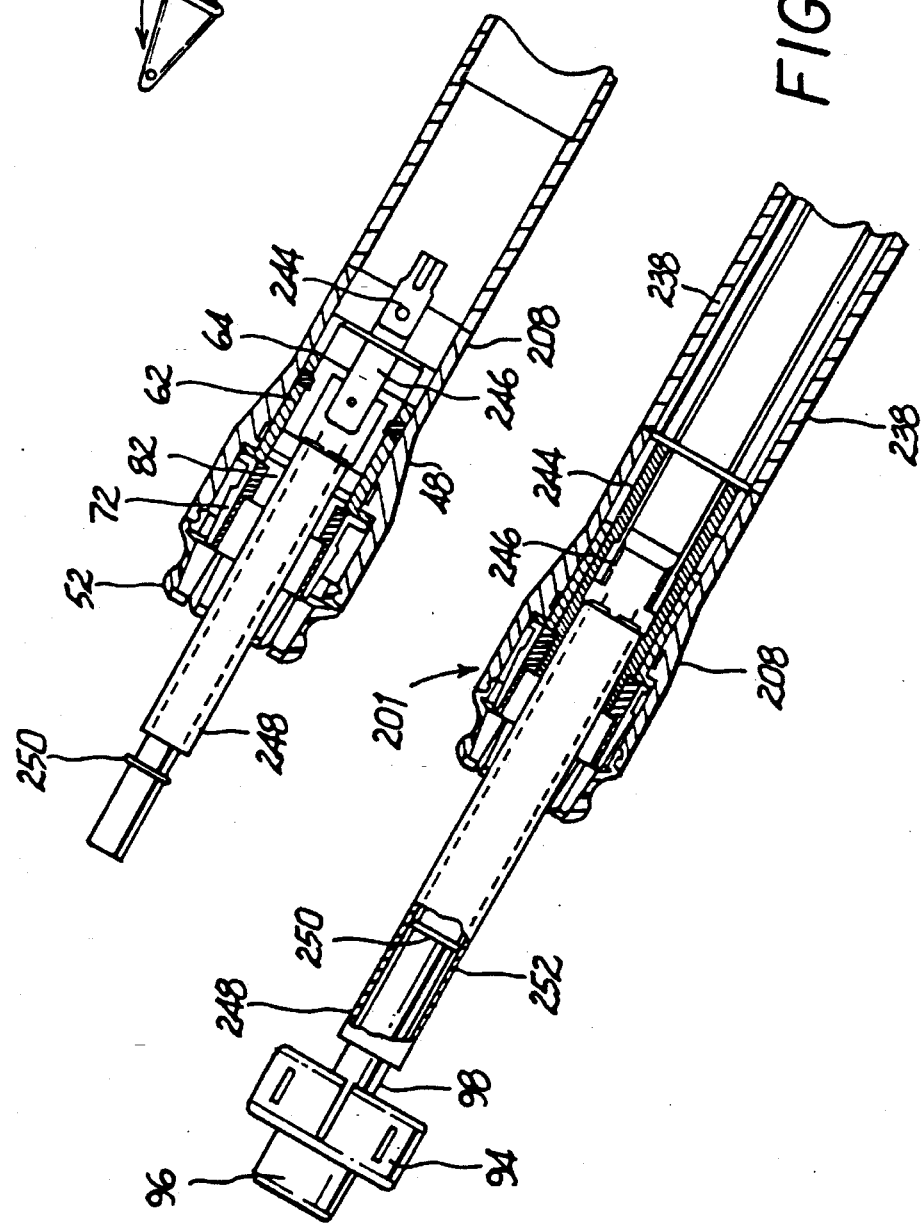

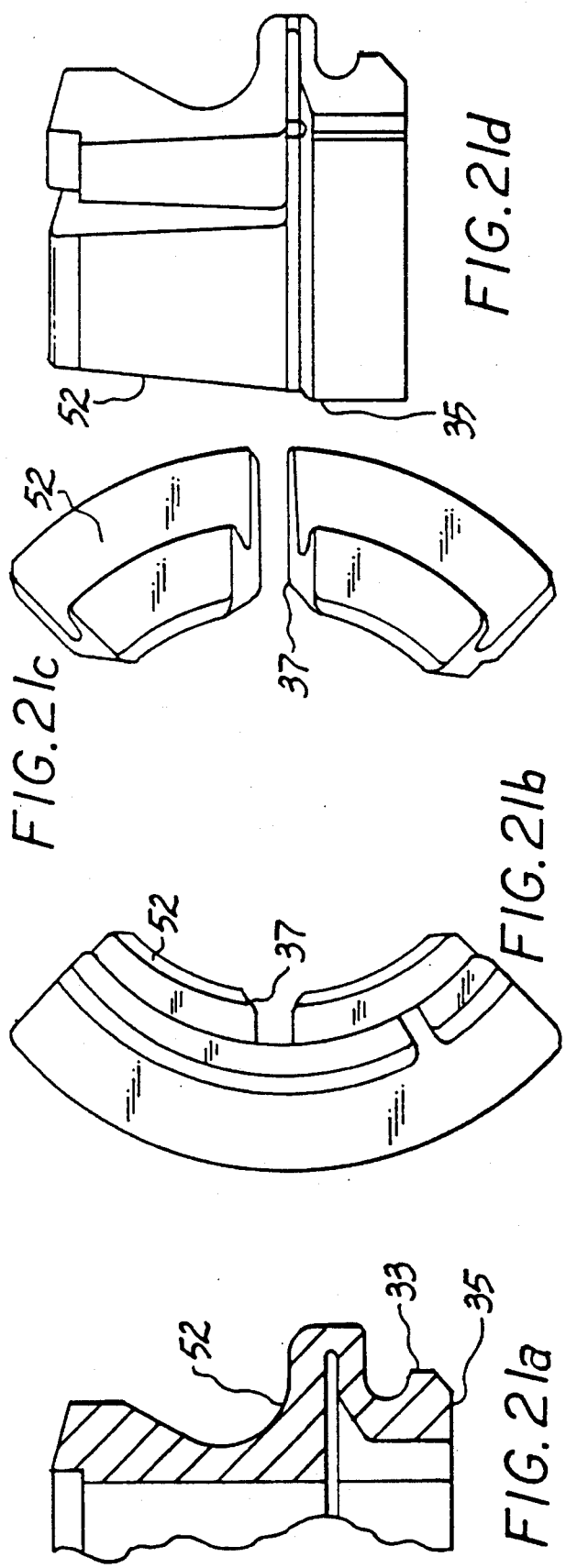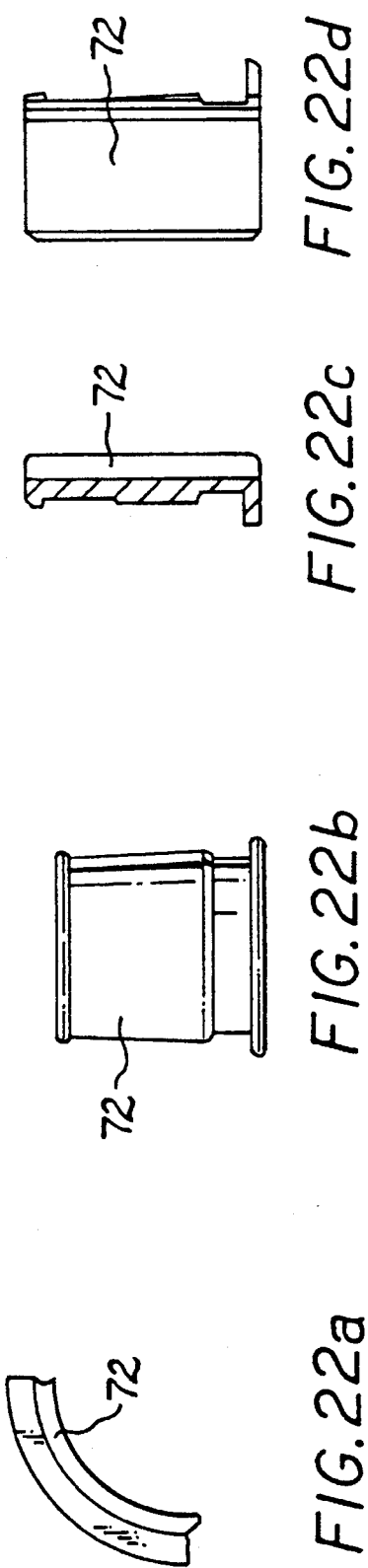

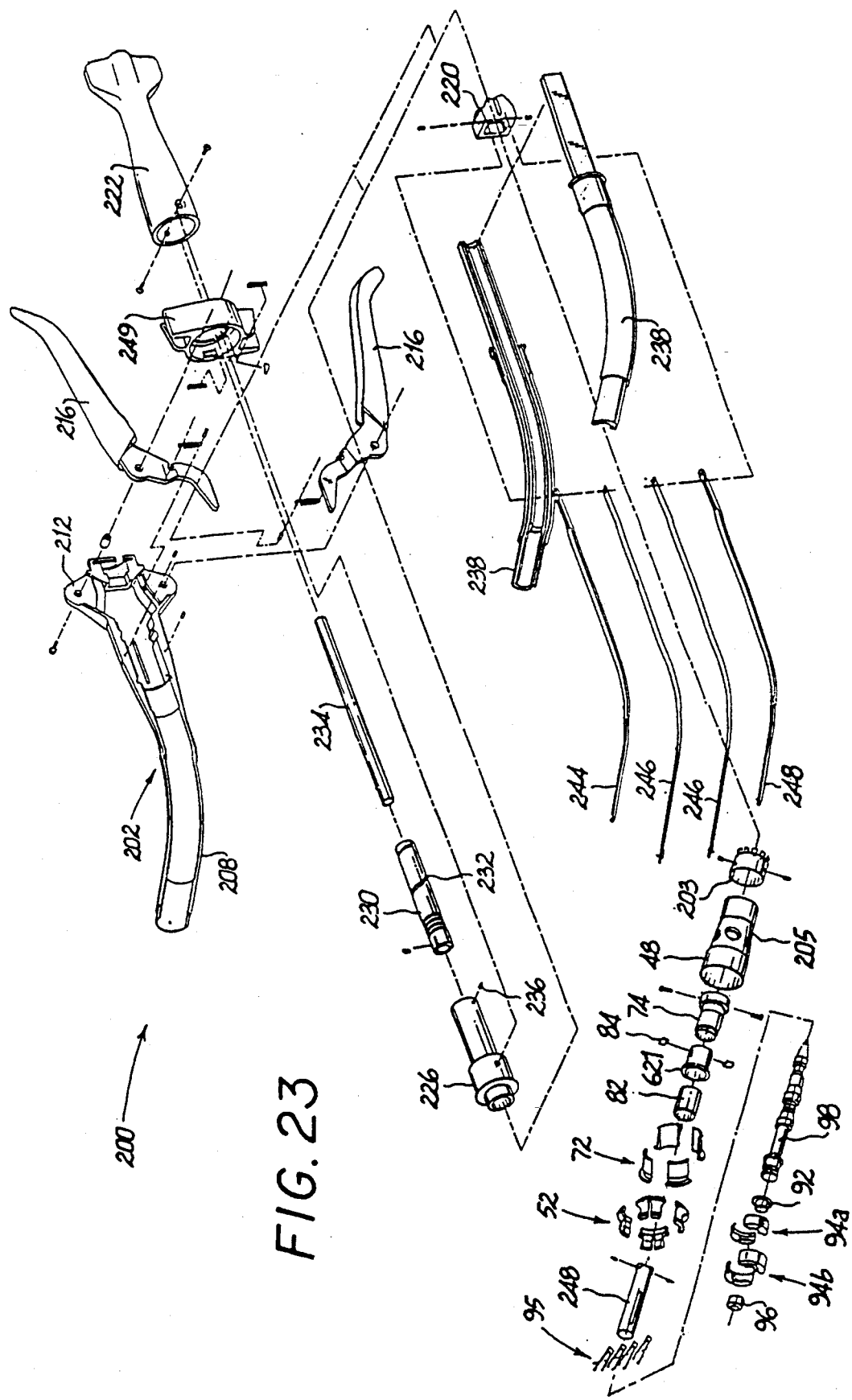

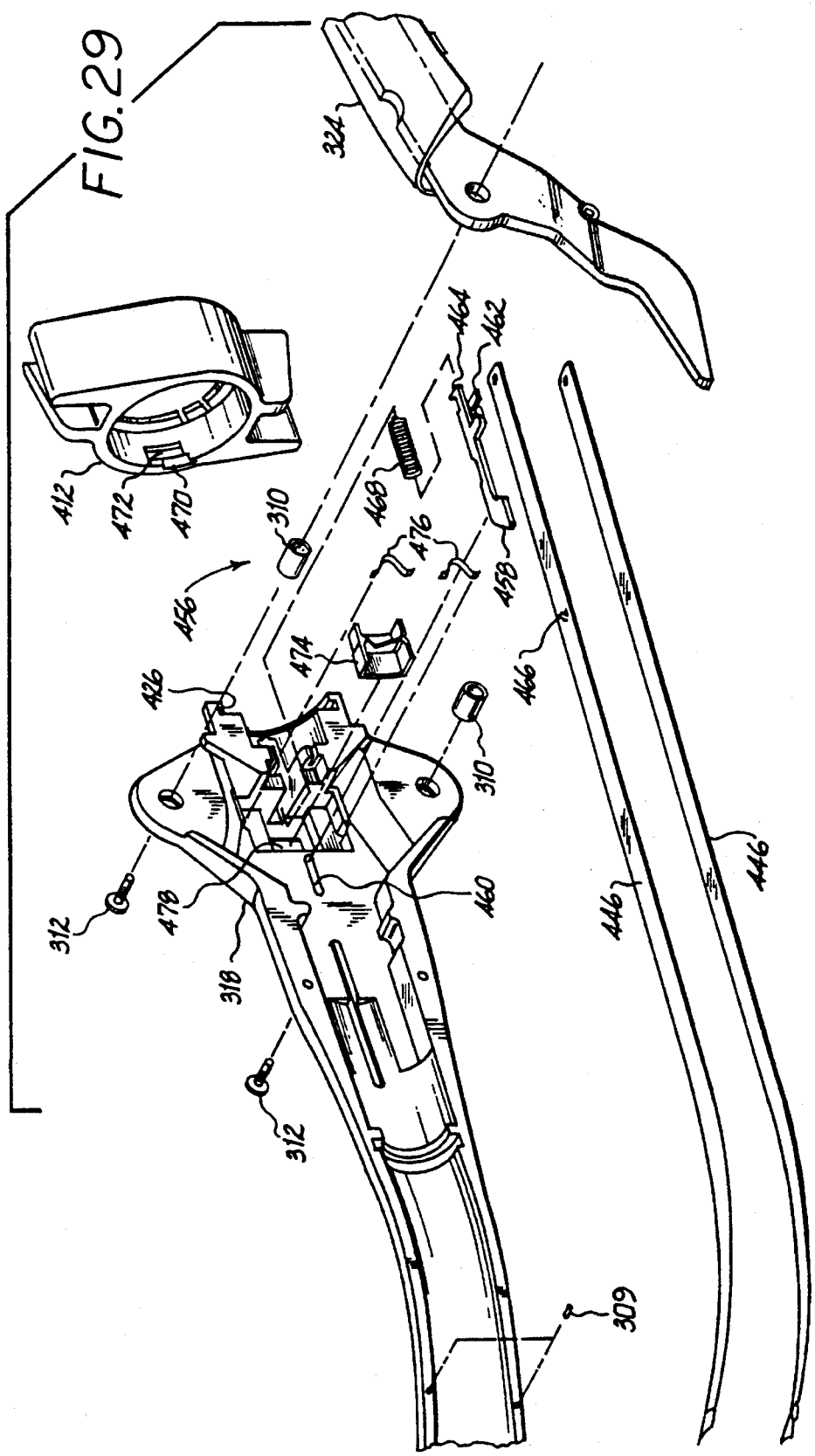

FRAGMENTABLE RING APPLIER

CROSS REFERENCE TO RELATED APPLICATION

This application is a continuation-in-part of prior application Ser. No. 07/959,152, filed Oct. 9, 1992, now U.S. Pat. No. 5,376,098, incorporated herein by reference.

BACKGROUND OF THE INVENTION

1. Field of the Invention

The present invention relates to surgical instruments used to perform circular anastomosis of tubular tissue sections and, more particularly, to a surgical instrument suitable for installation of multi-ring compression devices for circular anastomosis of tubular tissue sections.

2. Description of Related Art

Some surgical procedures, such as repair of the colon, require the joining of two rather large sections of tubular tissue. During these procedures, a diseased area of tissue is excised leaving two free ends of healthy tissue to be joined. Some known methods of joining the tissues include stapling or suturing the ends together. A more recent advancement in the art, called a multi-ring compression device, is used to clamp the free ends of the tissue between a series of interlocking rings whose centers are then cut away.

Typically, a multi-ring compression device consists of an outer ring assembly which fits over an intermediary ring. The two rings are then locked together by inserting an inner ring in the intermediary ring which locks in place.

In use the free open ends of tissue are captured between the outer ring assembly and the intermediary ring. The entire assembly is then locked together by insertion of the inner ring. The inner core of the ring assembly is then cut away along with any excess tissue. The clamped tissue within the rings is deprived of blood causing necrosis to take place. The outer tissue heals while the necrosised inner tissues and clamps are detached and expelled by the body. Newer clamps or compression rings, such as those shown in U.S. Pat. No. 4,966,602, have a fragmentable structure which enhances the bodies ability to expel the device.

Various surgical instruments have been developed to install the multi-ring compression devices. One known surgical instrument used to install the compression rings is shown in U.S. Pat. No. 4,681,108 to Rosati et al. This instrument generally comprises a cylindrical housing having means for aligning the rings within the tubular tissue sections, driving means for clamping the rings together in locking arrangement around the tissue sections and cutting means for removing excess tissue ends and detaching the instrument from the rings. In the Rosati et al. instrument, the cutting means consists of an advancing circular blade which both cuts the tissue and rings and pushes the rings free of the instrument in one continuous stroke.

Another known instrument for installing multi-ring compression devices is shown in U.S. Pat. No. 4,907,591 to Vasconcellos et al. This instrument includes such features as a rotating cutting blade and locking means to isolate the operation of aligning and clamping the rings from the separate continuous operation of cutting the excess tissue and freeing the instrument from the tissue.

Still other instruments, such as the flexible bronchoscope shown in U.S. Pat. No. 4,880,015 to Nierman, include provisions for insertion of accessory instruments such as biopsy forceps through the instrument in order to access the operative site. U.S. Pat. No. 4,817,847 to Redtenbacher discloses a circular stapling device having a removable anvil head provided with means to attach an endoscope to the anvil head.

SUMMARY AND OBJECTS OF THE INVENTION

The ring applier of the present invention is a novel surgical instrument suitable for insertion and assembly of multi-ring compression devices for circular anastomosis of tubular or hollow organ tissue sections such as, for example, the stomach, colon, etc. The instrument comprises a body having means to support and align the rings, means for clamping the rings around the free ends of the tissue sections, means for coring away excess clamped tissue and the centers of the rings, separate means for releasing the clamped rings from the instrument and dwell means to delay releasing the rings until after the coring operation is complete. The instrument may additionally include means for detaching a portion of the support means to facilitate installation and alignment, safety means to ensure safe operation and means for supplying various knife blade profiles.

In a preferred embodiment of the invention the dwell means consists of an external cup containing separate and coaxial elements for the channeling means and the releasing means. The external cup, channeling and releasing elements are provided with a series of recesses which, in cooperation with a plurality of shifter keys, act to separate the operations of coring the excess material and ring centers from the separate operation of releasing the assembled and cored rings from the instrument. In other embodiments the shifter keys are flexibly affixed to the releasing means.

In another embodiment of the invention the support means for supporting the outer ring assembly is detachable from the rest of the instrument. By detaching the outer ring and its support, it is more easily placed in a free open end of tubular tissue. The instrument can then be inserted in the opposing open end of tissue and thereafter reattached to the outer ring support means.

In a further embodiment of the invention the clamping means includes a handle which is rotatable with respect to said support means. A cam-clamp having a variable helical depression is attached to the support means and slidably supported within the handle such that rotation of the handle moves the cam-clamp within the handle. Preferably the variable helical depression in the cam-clamp is initially of a slow rate of twist to provide rapid initial approximation of the rings and of a rapid rate of twist towards the end of the cam-clamp travel to provide slower more precise approximation and increased torque for final clamping of the rings.

In still another embodiment of the invention a continuous bore extends longitudinally throughout the length of the instrument to provide a passageway for accessory instruments such as, for example, endoscopes, graspers, cutters and the like.

Additionally, lockout means may be provided to prevent coring of the tissue sections until they have been clamped.

Thus it is an object of the present invention to provide a novel surgical instrument capable of delaying the release of an assembled multi-ring compression device until after a coring operation has been completed.

It is a further object of the invention to provide novel means of detaching an outer ring support from the main body of the device to facilitate installation and alignment of the device.

It is a still further object of the invention to provide cutting means having various blade profiles.

Yet another object of the invention is to provide a safety device to prevent the instrument from being operated prematurely.

Another object of the invention is to provide venting means to prevent excessive pressure buildup in the device during clamping of the rings about tissue.

Other novel features and objects of the invention will become evident from the following detailed description of the invention.

BRIEF DESCRIPTION OF THE DRAWINGS

Preferred embodiments of the invention are described hereinbelow with reference to the drawings wherein:

FIGS. 14a, 14b and 14c are views of various knife blade profiles;

FIGS. 17a, 17b, 17c and 17d are top and side detail views of one variation of the external cup including associated trocar tip and center rod;

FIGS. 18a, 18b, 18c and 18d are detail views of other varying external cup portions of the alternative embodiment incorporating another variation of the detachable outer ring support and associated trocar tips;

FIGS. 21a, 21b, 21c and 21d are detail views of an intermediate ring;

FIGS. 22a, 22b, 22c and 22d are detail views of an inner ring;

FIG. 23 is an exploded perspective view of the alternate embodiment of the invention;

FIG. 28 is a partial plan view of a band attachment means;

FIG. 29 is an enlarged exploded view of a lockout mechanism utilized in the device of FIG. 24;

DETAILED DESCRIPTION OF THE INVENTION

Figure 1:
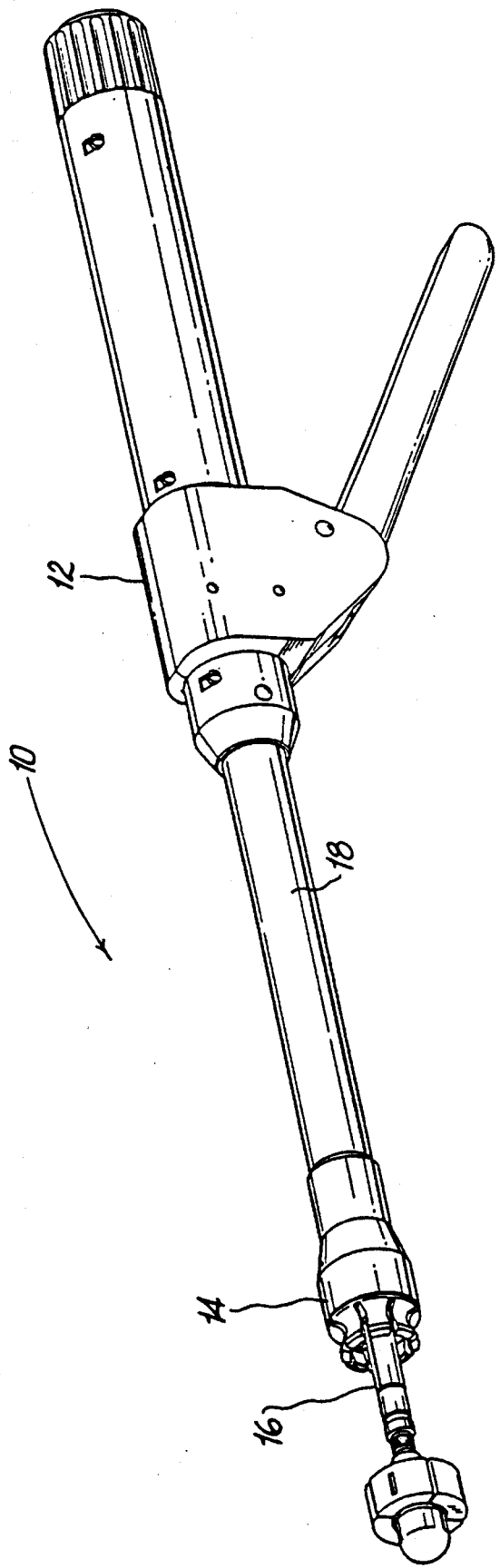
FIG. 1 is an overall perspective view of one embodiment of the present invention.

With reference now to the drawings wherein like numerals represent identical parts throughout the several views, and more particularly with reference to FIG. 1, the ring applier 10 generally includes a body portion 12, a head portion 14 and a retractor portion 16 extending through body portion 12 and head portion 14. An external tube 18 joins head portion 14 to body portion 12.

Figure 2:
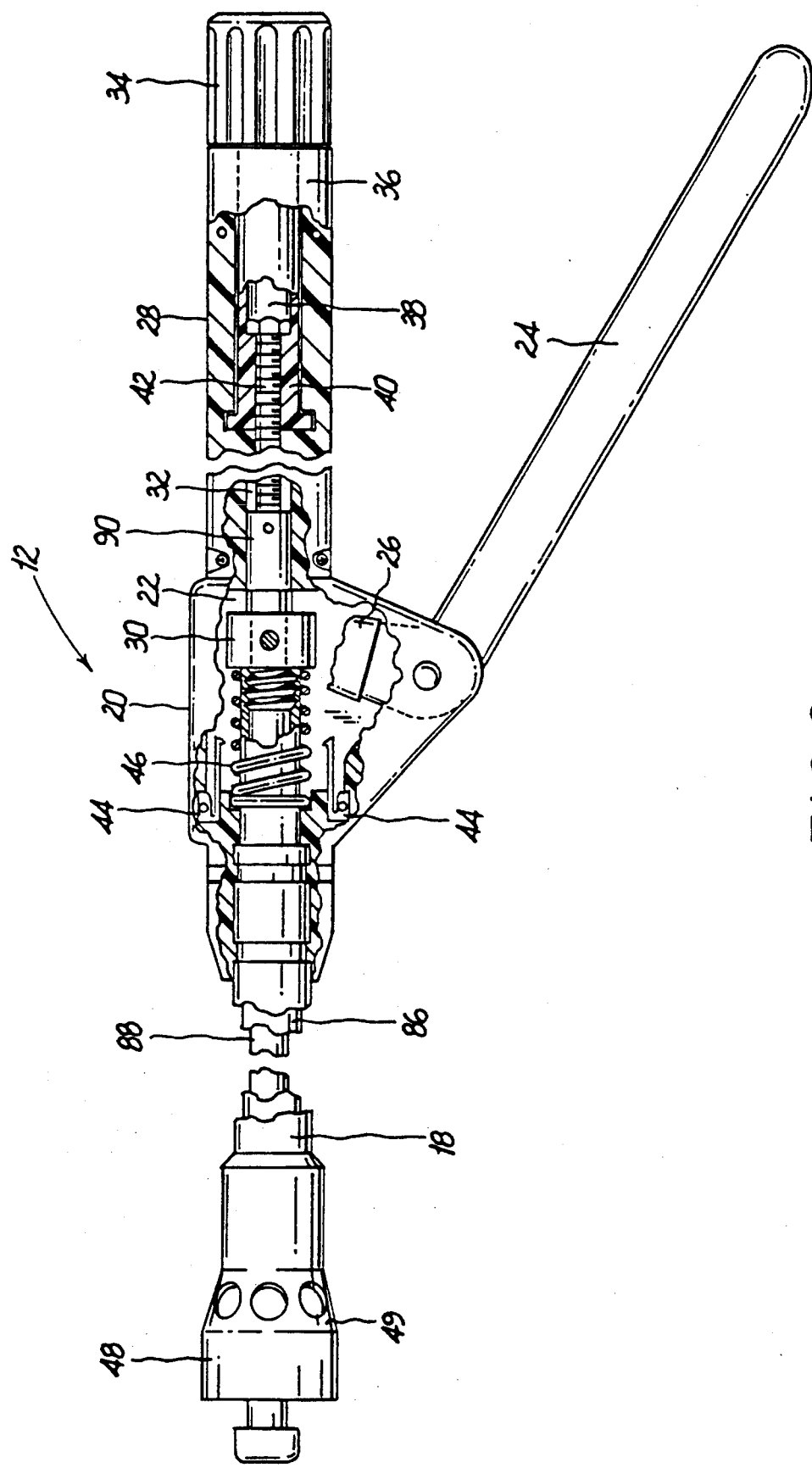
FIG. 2 is an enlarged side detail view of the handle portion of one embodiment of the present invention.

As shown in FIG. 2, body portion 12 further includes a saddle member 20 having a bore 22 therethrough, an L-shaped handle 24 pivotably mounted on saddle member 20 and having an end 26 extending into bore 22, and a tail member 28 extending outward from saddle member 20. Saddle member 20 includes a threaded collar 30 slidably disposed within bore 22 and pivotally connected to inward extending end 26 of handle 24 such that movement of handle 24 slides collar 30 within saddle bore 22. It is further contemplated to provide locking springs 44 designed to hold collar 30 at the end of its forward travel. Saddle member 20 further includes a return spring 46 for biasing collar 30 rearward within saddle bore 22.

Tail member 28 extends outward from saddle member 20 and defines a bore 32 coaxial and communicative with saddle bore 22. A clamp knob 34 is rotatably suspended at one end 36 of tail member 28 and has a bore 38 coaxial with tail bore 32. Knob 34 has a threaded base section 40 in which a threaded shaft 42 is slidably suspended within bore 38 and in threaded engagement with knob 34 such that turning knob 34 moves shaft 42 within tail bore 32.

The multi-ring compression devices used in connection with ring applier 10 generally include a plurality of interlocking rings for clamping tissue therebetween. Typically these devices consist of an outer ring 94 and an intermediary ring 52 between which the tissue is clamped and an inner ring 72 for locking insertion into intermediary ring 52. The insertion of the inner ring 72 forces outward biased edges of the intermediary ring 52 against inside edges of the outer ring 94 for a press-fit connection. When the inner ring 72 is fully seated within the intermediary ring 52, an outward facing lip of the inner ring 72 locks into place on an annular recess on an inside edge of the intermediary ring 52 thus locking the entire assembly together.

Turning now to FIGS. 19–22, a preferred embodiment of the multi-ring compression device consists of fragmentable ring assemblies. The outer ring assembly 94 consists of a male fragmentable ring 94a (FIGS. 20 (a–e)), having a shoulder 21 on a rim 23 thereof, which fits over a similar female fragmentable ring 94b (FIGS. 19(a–e)). Rings 94a and 94b are each molded in two side-by-side halves to facilitate manufacture. Each half includes a semi-circular central hub 25 to allow capture on one end of ring applier 10. Rather than provide uniform hub thickness thin ribs 27 are incorporated into relatively less thick region of the hub 25. The ribs and less thick region make it easier for hub 25 to be cut free from the body and ring applier 10 as described hereinbelow. The sectional areas of the first ring are offset from the sectional areas of the second ring, the two rings being held together by an overlapping series of projections 29 on ring 94a and recesses 31 on ring 94b. Preferably, the projections 29 on ring 94a and recesses 31 on ring 94b are aligned with the molding plane to facilitate molding. The intermediary fragmentable ring 52 is fully sectioned and has an annular projection 33 at a base 35 thereof for mounting on ring applier 10. Slots 37 in the base projection facilitates ejection of the ring assembly from ring applier 10. The locking inner fragmentable ring 72 is also sectioned into four pieces and has male and female sides so the pieces can lock together. The preferred version is more easily molded in the manufacturing process than other known versions and incorporates fillets (internal) and radii (external) on all parts to avoid sharp corners. Preferably the rings are formed of a nylon or polycarbonate material such as Lexan®, available from General Electric Corporation. Additionally, it is preferable to form the rings with approximately 3%–15% barium-sulfate to enhance the detectability of the rings by X-rays.

Figure 4:
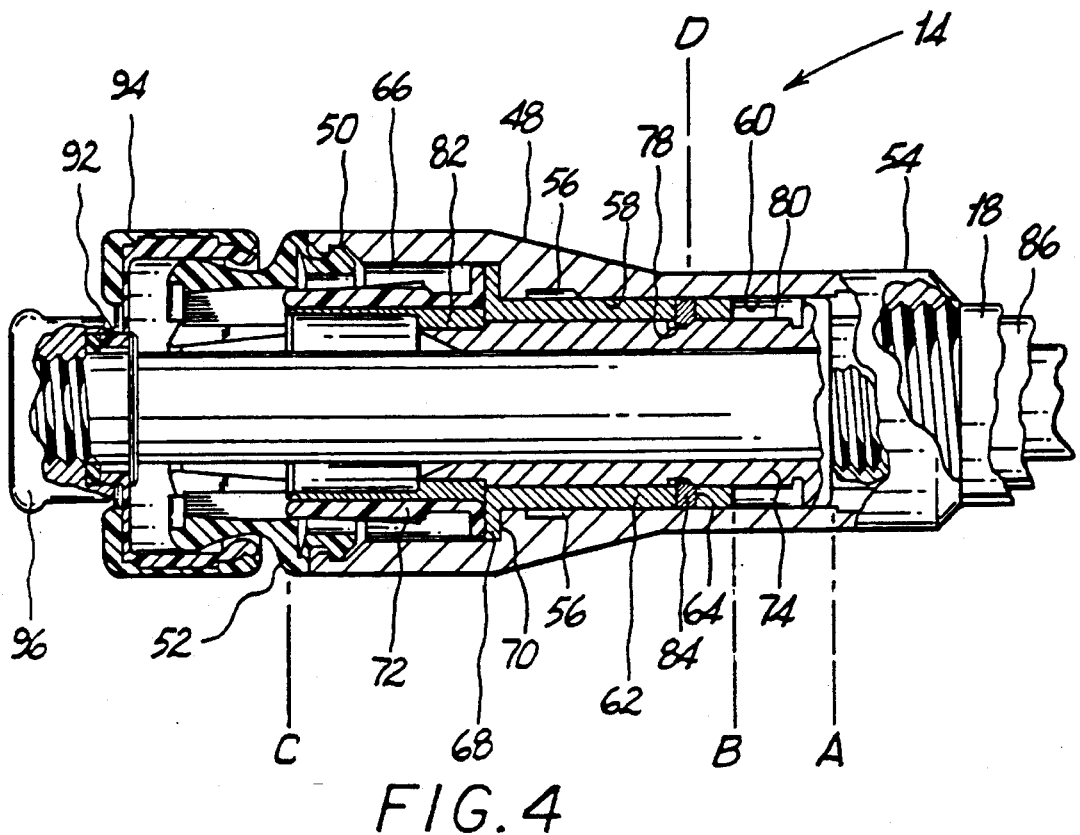
FIG. 4 is an enlarged side detail view of the head portion of the instrument of FIG. 1 showing retraction of an outer ring over an intermediary ring.

Referring now to FIG. 4 head portion 14 comprises an external cup 48 having a grooved distal end 50 for support of intermediary ring 52 and is threadably engagable with external tube portion 18 at a proximal end 54 of cup 48 thereof. External cup 48 may be provided with venting means including a plurality of vent holes 49 to allow escape of excess pressure built up during clamping of tissue. The venting means may be similar to that used in U.S. Pat. No. 4,304,236 to Conta et al., the disclosure of which is incorporated herein by reference. External cup 48 further includes a plurality of dwell recesses 56 located on an inner surface 58 of external cup 48 and disposed within a restricted bore section 60 of external cup 48. A pusher 62 having shifter key channels 64 is slidably disposed within an enlarged bore area 66 of external cup 48 and has a circumferential flange 68 at a distal end which abuts a restricted edge 70 of restricted bore section 60. Pusher 62 slidably supports inner ring 72.

A knife holder 74 having a circumferential flange 76 at a proximal end is slidably disposed within pusher 62. Knife holder 74 further includes a plurality of shifter key recesses 78 on an outer surface 80 and means for support of a circular knife blade 82 affixed to a distal end of knife holder 74. A plurality of shifter keys 84 reside in shifter key channels 64.

Figure 8A:
FIGS. 8a and 8b are side and top detail views of the shifter keys.
Figure 8B:
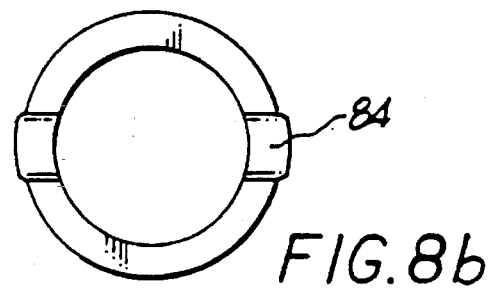

Referring to FIGS. 8a and 8b, in the preferred embodiment, shifter keys 84 have a generally trapezoidal cross section along an arcing longitudinal axis. However, one skilled in the art will appreciate that other cross-sectional configurations may be substituted therefor.

A knife tube 86 is coaxial with and slidably supported within external tube 18. (See FIGS. 2 and 3.) Knife tube 86 is threadably engaged with collar 30 at a proximal end and threadably engaged with knife holder 74 at a distal end thereof such that movement of handle 24 causes knife holder 74 to slide within pusher 62 thereby transmitting the movement of handle 24 to pusher 62.

Figure 3:
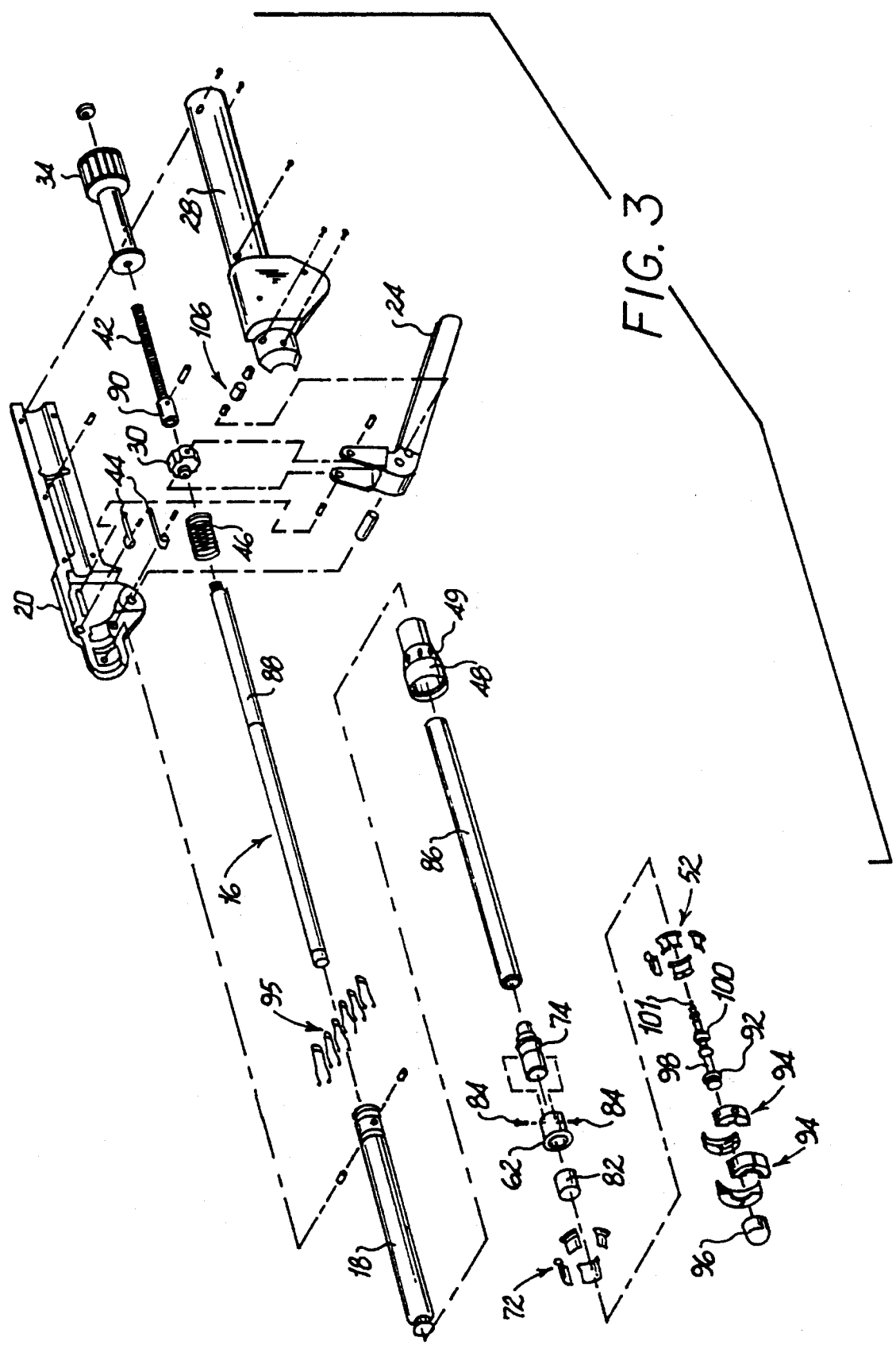
FIG. 3 is an exploded perspective view of one embodiment of the present invention.

Referring to FIG. 3 retractor portion 16 includes a clamp rod 88 affixed at a proximal end to a coupling 90 to transmit motion of shaft 42 through tube 18 to coupling 90. Coupling 90 resides in tail member 28 and is engagable with threaded shaft 42. Clamp rod 88 has an annular projection 92 at a distal end thereof for carrying outer ring 94. Clamp rod 88 further includes a threaded retainer 96 to hold outer ring 94 in place against annular projection 92.

In a preferred embodiment of the invention retainer 96 and annular projection 92 are located on a center rod 98 which is detachable from said clamp rod 88. Referring to FIG. 3, center rod 98 has an annular projection 100 disposed proximally along its length. At the extreme proximal end of center rod 98 is a pointed tip 99 having a hole 101 therein for attachment of a suture or thread. In this preferred embodiment clamp rod 88 is hollow at a distal end thereof. An annular slot 102 is located on an inner surface of clamp rod 88 and is supplied with a plurality of leaf springs 95 biased inward into depression 102 for snap-fit receipt of annular projection 100 on center rod 98.

Figure 10:
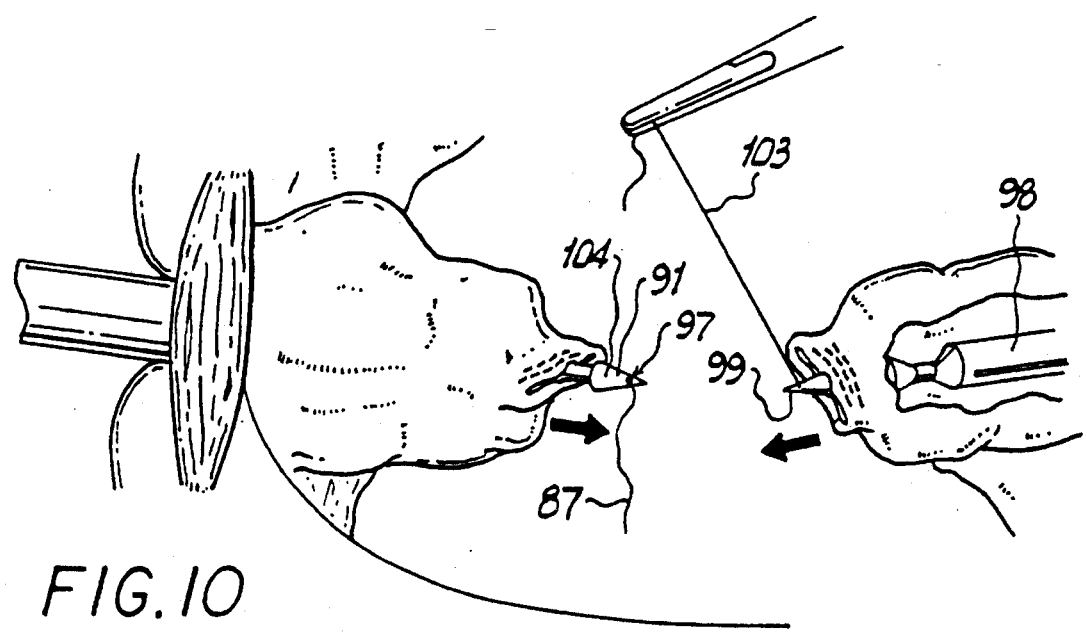
FIG. 10 is a perspective view showing the trocar points pulled through the stapled edges of the tissue.
Figure 11:
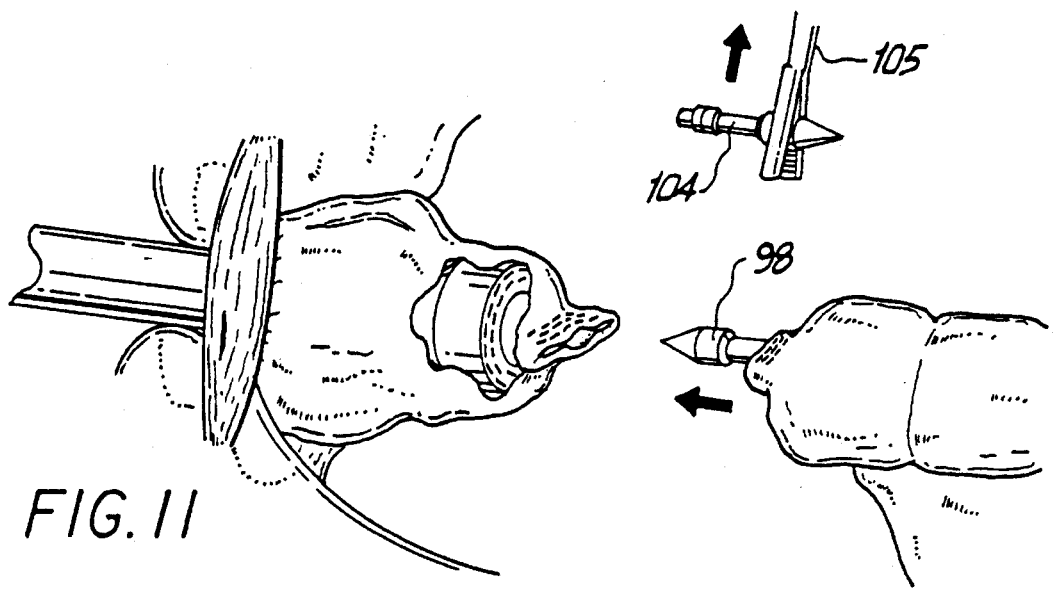
FIG. 11 is a perspective view showing a detachable trocar point being removed by grippers.

Referring to FIGS. 10 and 11, in this embodiment there is also provided a pointed trocar tip 104 having a suture or thread retaining hole 97 at a point 91 and an annular projection 93 at a proximal end thereof for snap fit insertion in the annular slot 102 of clamp rod 88.

In still a further embodiment of the invention a safety button 106, FIG. 3, is provided on saddle 20 for preventing handle 24 from being prematurely closed.

As can be seen in FIGS. 14(a–c) the knife blade 82 may have several cutting profiles designed to optimize a particular cutting operation. In these embodiments the leading edge of the knife blade 82 may have a flat shape such as blade 82a (FIG. 14a), a sinusoidal shape such as blade 82b (FIG. 14b) or a hyperbolic shape such as blade 82c (FIG. 14c). It is within the contemplated scope of the invention to use varying knife blade profiles not limited to those shown herein.

Referring now to FIGS. 2–13 the sequence of operation of the present invention will now be described. In preparing ring applier 10 for use, outer ring 94 is placed over projection 92 of clamp rod 88. Retainer 96 is threaded over outer ring 94 securing outer ring 94 to clamp rod 88. Inner ring 72 is inserted into enlarged area 66 and abuts flange 68 of pusher 62. Intermediary ring 52 is then press fit into the grooved distal end 50 of external cup 48. In this manner, the ring applier 10 is readied for use.

Figure 9:
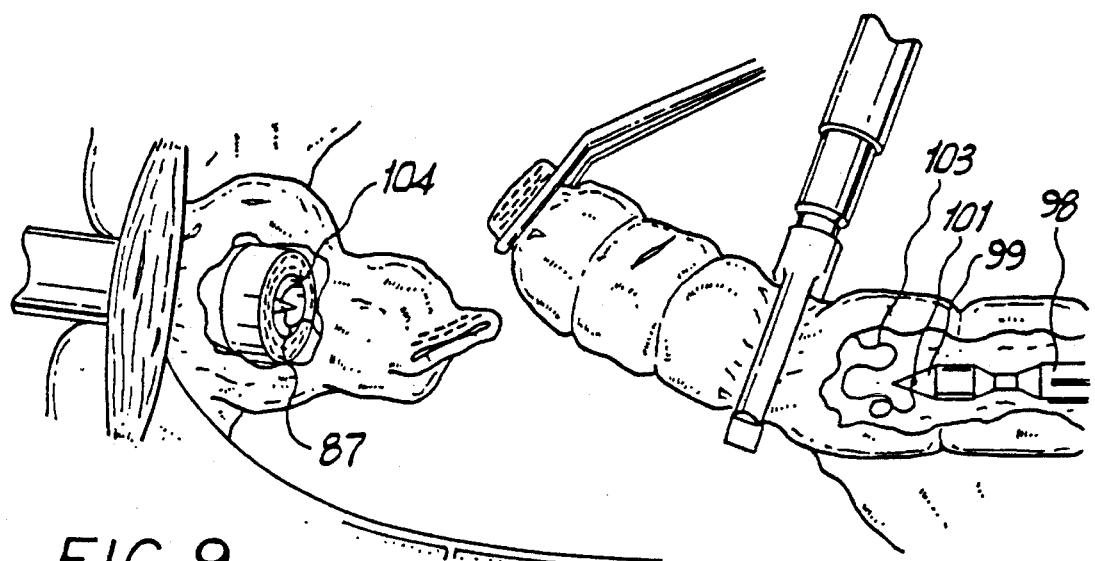
FIG. 9 is a perspective view of a diseased section of the colon being excised and showing a detachable portion of the instrument deployed in a distal section of the colon.

In a preferred use of the invention the detachable center rod 98 assembly including outer ring 94 and retainer 96, and a trailing suture 103 attached to a hole 101 of center rod tip 99, would have been inserted into a healthy section of tubular or hollow organ tissue and located distally from the diseased tissue as shown in FIG. 9. As further shown in FIG. 9, the diseased tissue would then be excised by known methods. One such method utilizes a separate stapling device to apply several staggered rows of staples to an area of healthy tissue on either side of the diseased tissue and cut and remove the now stapled "packet" of diseased tissue leaving two healthy free ends of tissue stapled closed.

Referring to FIG. 10, a small incision would then be made to grasp trailing suture 103 and pull pointed tip 99 of center rod 98 through the distal stapled section of tissue. With trocar tip 104 snap fit into place on clamp rod 88, tip 104 would be inserted up to the opposing proximal stapled tissue end and pulled through the staples by a suture 87 affixed to hole 97 in point 91 in the same manner as above, as best seen in FIG. 17a.

Figure 12:
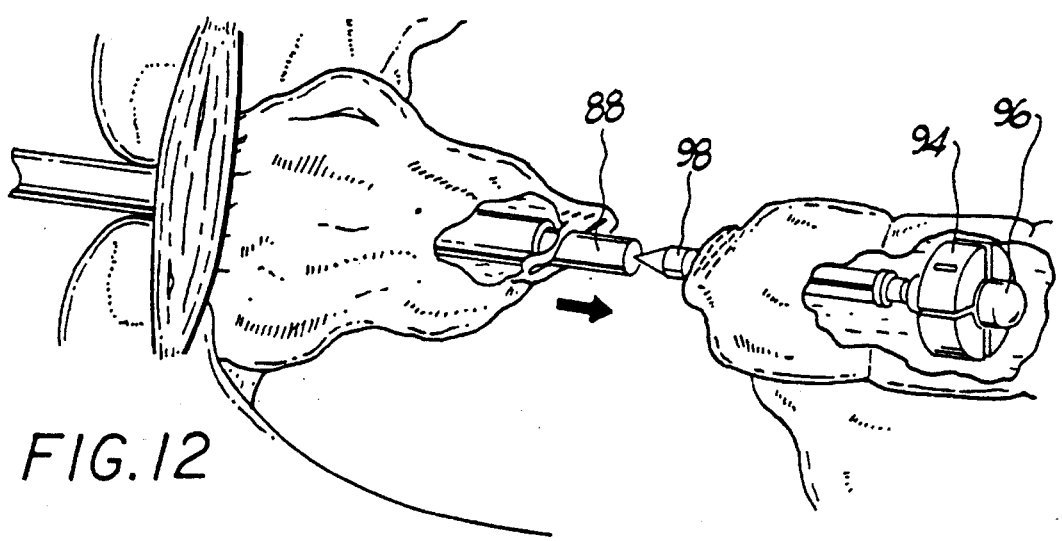
FIG. 12 is a perspective view showing the detachable assembly being attached to the instrument.
Figure 13:
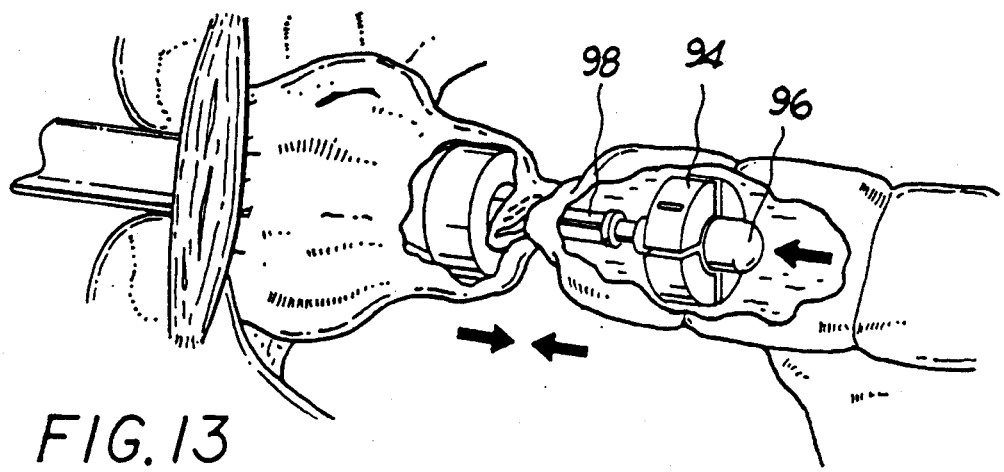
FIG. 13 is a perspective view of the colon just prior to clamping the ring assemblies.

As shown in FIG. 11, trocar tip 104 can then be removed from clamp rod 88 by grippers 105 or other known methods, after which clamp rod 88 is then snap fit over the proximal end of center rod 98 to attach center rod assembly 98 to clamp rod 88 of ring applier 10 FIGS. 12 and 13.

Once the two rods, 88 and 98, have been joined, with the stapled free ends of tubular tissue now located between outer ring 94 and intermediary ring 52 the clamp rod 88 is retracted by turning the clamp knob 34 which draws the threaded shaft 42 and thus the clamp rod 88 rearward. Drawing clamp rod 88 rearward pulls outer ring 94 over intermediary ring 52 thus clamping the free ends of the tubular tissue sections between rings 94 and 52.

The remaining operation can best be easily understood in stages wherein FIG. 4 is stage one showing outer ring 94 fully retracted over intermediary ring 52. The free ends of the tissue sections (not shown) would be captured between the rings 52 and 94. At the end of stage one the center of outer ring 94 and the excess tissue are ready to be cored by knife blade 82. In this stage it can be seen that pusher 62 and knife holder 74 are disposed fully to the rear of external cup 48 and shifter keys 84 reside between shifter key channels 64 in pusher 62 and shifter key recess 78 on knife holder 74. The positions of the base of knife holder 74 are indicated by reference letter A, the base of the pusher 62 by reference letter B, the forward edge of the knife blade 82 by reference letter C and the position of the shifter keys 84 are indicated by reference letter D.

Figure 5:
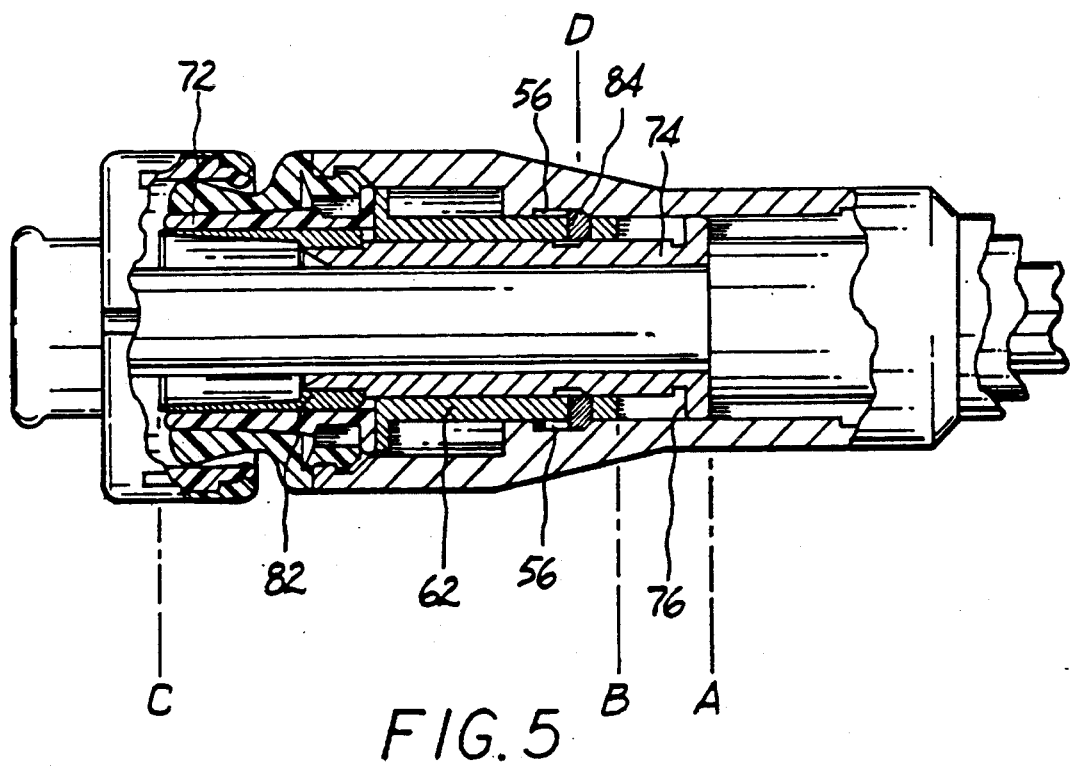
FIG. 5 is a similar view thereof showing insertion of an inner locking ring into said intermediary ring.

When the handles 42 are pivoted inward after the first stage knife tube 86 moves pusher 62 and knife holder 74 together as a unit, connected by said shifter keys, forward. Pusher 62 thus moves inner ring 72 forward into locking engagement with intermediary ring 52 at which point (stage 2) the shifter keys 84 are forced out of shifter key recesses 78 and into dwell recesses 56 (Reference point D) due to the angles on the edges of shifter keys 84 and shifter key recesses 78. As can be seen in FIG. 5, at the end of the second stage the end of pusher 62 (reference point B) and the end of the knife holder 74 (reference point A) are still spaced apart.

Figure 6:
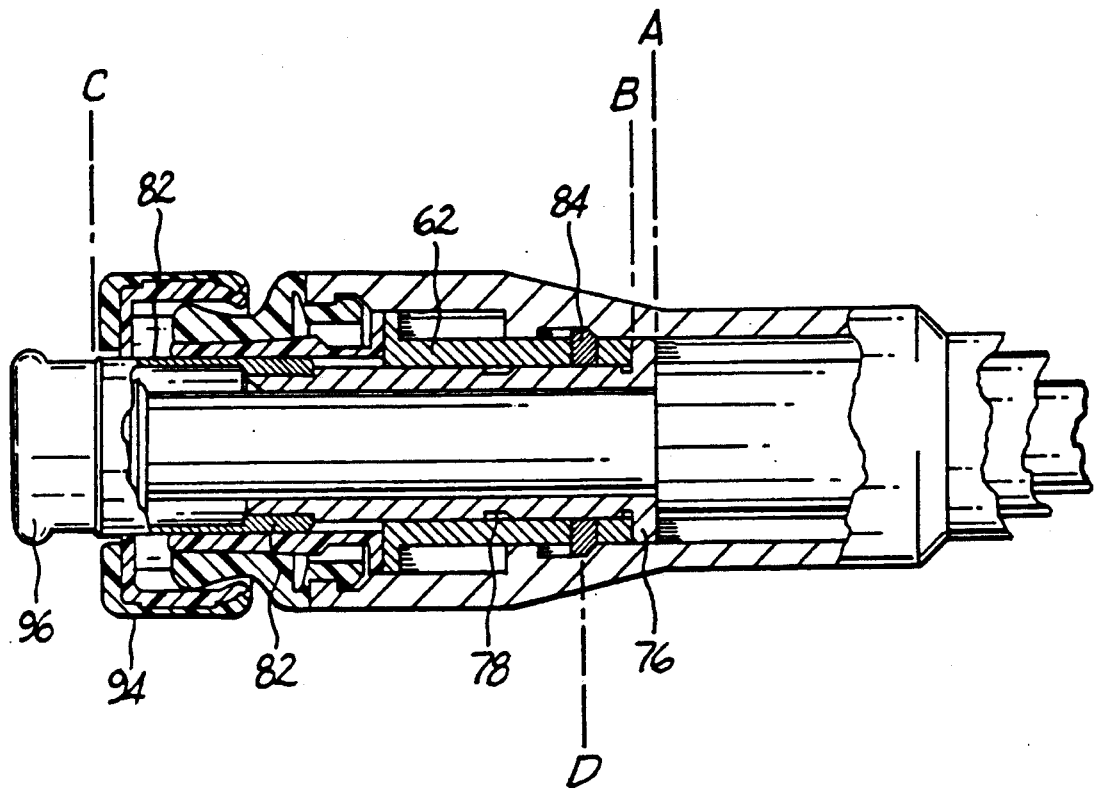
FIG. 6 is a similar view thereof showing the advancement of the coring means through the outer ring.

Referring to FIG. 6, in stage 3 handles 24 continue to pivot and knife tube 86 advances knife holder 74, independent of pusher 62 which is disengaged from knife holder 74, until rear flanges 76 on the knife holder 74 abut the rear edge of the pusher 62 (reference point B). During stage 3 advancing knife holder 74 advances knife blade 82 (reference point C) through the captured excess tissue and through the portion of outer ring 94 held by retainer 96 thus fully coring the multi-ring clamp assembly to provide a clear passageway therein.

It will be noted that with shifter keys 84 positioned in dwell recess 56 there is nothing to advance the pusher 62 until the end of stage 3 wherein the knife holder flange 76 abuts the rear end of pusher 62.

Figure 7:
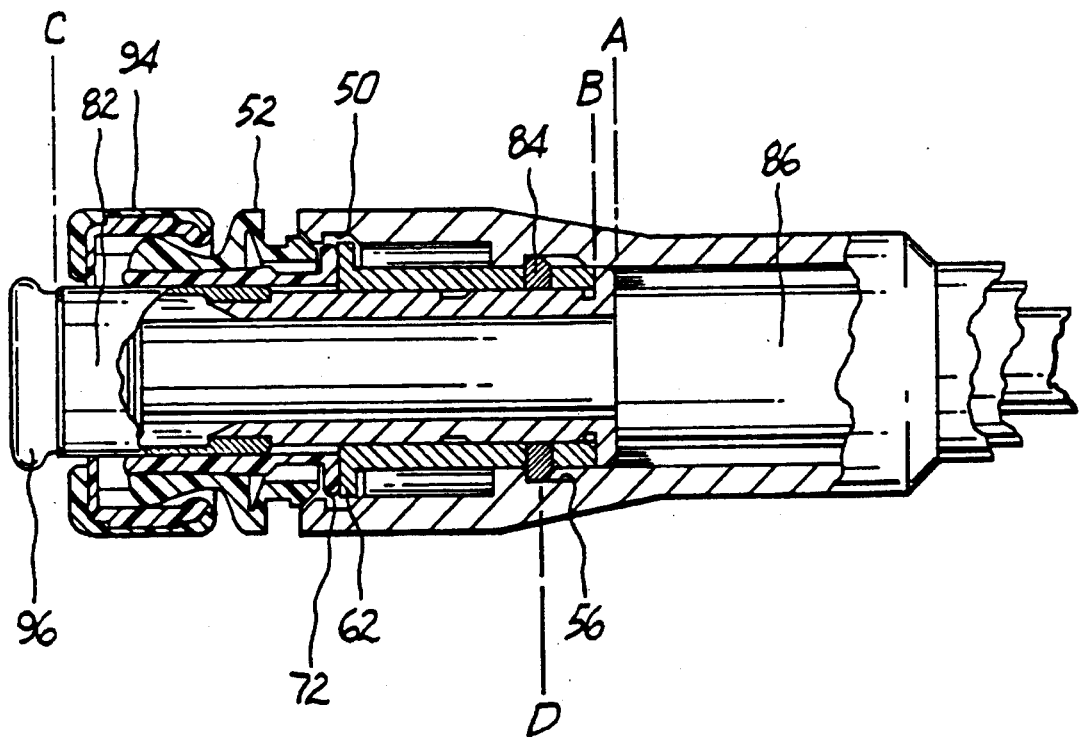
FIG. 7 is a similar view thereof showing the release of the coupling assembly from the present invention.

Finally, as can best be seen in FIG. 7 (stage 4) as handles 24 are pivoted fully closed flange 76 of knife holder 74 (reference point A) is moved forward by knife tube 86 carrying with it pusher 62 (see reference point B). Shifter keys 84 now move forward in dwell recesses 56 allowing pusher 62 to finally push the assembled rings free of the annular holding groove 50 on external cup 48. At this point the rings have been fully assembled about the free ends of the tissue sections, excess tissue and the center of outer ring 94 have been cored out leaving a clear passageway therein and the assembled rings are freed from ring applier 10. Thus the use of the shifter keys and dwell recesses allows the coring operation to be fully complete before the ring assembly is pushed free of the instrument. Ring applier 10 can now be removed. Eventually the clamped tissue will necrotize while the tubular tissue ends heal together. The necrotized tissue and ring assembly will then detach from the healthy tissue and be expelled from the body.

As described above, the ring assembly may be of the fragmentable variety to facilitate expulsion. Furthermore, whether of the solid or fragmentable variety, the ring assembly may be partially or wholly formed of degradable or bio-absorbable materials which are degraded or absorbed over time as the tissue heals leaving less or no clamp material to be expelled by the body. However, as noted above, the preferred material is nylon or polycarbonate, e.g. Lexan®.

Figure 15:
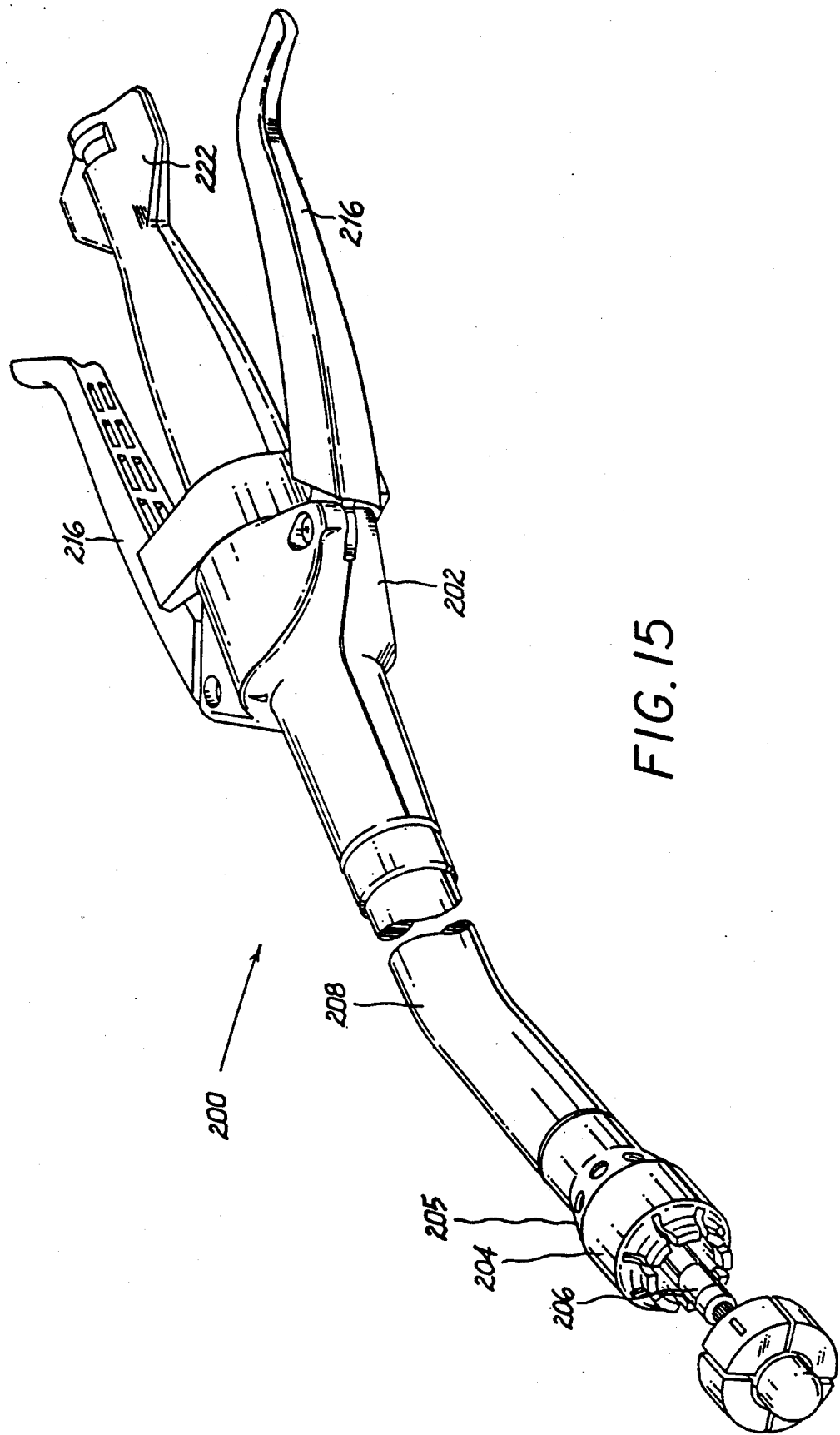
FIG. 15 is a perspective view showing an alternate double handle embodiment of the present invention.

An alternative embodiment of the present invention is illustrated in FIGS. 15 and 23 wherein ring applier 200 generally includes a body portion 202, a head portion 204 and a retractor portion 206 extending through body portion 202 and head portion 204.

As shown in FIGS. 15 and 23, body portion 202 is comprised of an elongated front end tube 208, preferably curved, having a bore 210 therein and a wing shaped back end 212 having a bore 214 coaxial with bore 210. Body 202 includes a pair of handles 216, pivotally and opposingly mounted on body wing 212, having inwardly extending front ends 218 extending into wing bore 214. A knife cam 220 is slidingly disposed within wing bore 214 and in abutting contact with inwardly extending front ends 218 such that pivoting handles 216 inward forces knife cam 220 forward within wing bore 214.

Body portion 202 further includes a tail member 222, defining a bore 224 coaxial and communicable with wing bore 214, which extends backwards from body wing 212 and is centered between opposing handles 216. A barrel 226, defining a bore 228, is rotatably attached to body wing 212 at a first end and is rigidly affixed to tail bore 224 at a second end for rotatable support tail member 222 on body wing 212.

A cam-clamp 230 having a variable helical depression 232 on an outer surface thereof, and defining a bore 233 is rotatably suspended within barrel bore 228. The variable helical depression 232 in cam-clamp 230 is initially of a slow rate of twist at a proximal end of cam-clamp 230 to provide a rapid initial approximation of rings 52 and 94. At the distal end of cam-clamp 230 the helical depression 232 changes to a rapid rate of twist to provide slower more precise approximation of rings 52 and 94 and to provide increased torque for clamping rings 52 and 94 around ends of tubular tissue sections.

A guide tube 234 is affixed to wing body 212 at a first end and extends through bore 233 on cam-clamp 230 into tail bore 224 to guide cam-clamp 230 within tail bore 224.

A guide pin 236 is rigidly affixed to barrel 226 at a proximal end thereof and extends into barrel bore 228 such that a free end of pin 236 engages the helical depression 232 of cam-clamp 230. By rotating tail member 222, barrel 226 drives pin 236 in helical depression 232, thereby drawing cam-clamp 230 along guide rod 234 initially at a fast rate and subsequently in a slower, stronger and more precise fashion. Typically, approximately 2–5 complete turns of tail member 222 is required to approximate rings 52 and 94.

Referring to FIGS. 17, 18 and 23 head portion 204 is similar to head portion 14 referred to above and contains the same parts/elements recited therein including pusher 62, knife holder 74, knife blade 82 and shifter keys 84 which function together in exactly the same manner recited hereinabove. Additionally, vent holes 205 (FIGS. 15 and 23) may be provided to prevent the buildup of excess pressures during clamping. As shown in FIG. 18a in one embodiment of ring applier 200 external cup 48 is integral with front end tube 208. In a second embodiment of ring applier 200, FIG. 18b, external cup 48 is partially integral with tube 208 and has a threadably detachable front portion 201 to facilitate insertion of the rings. In a third embodiment of ring applier 200, FIGS. 17a and b, external cup 48 is affixed to body tube 208 by a threaded sleeve-head 203 threaded into external cup 48.

As shown in FIGS. 17b, 18b and 23, a pair of abutting semicircular guide inserts 238 are disposed within tube bore 210 and extend therethrough. Each insert 238 has a pair of longitudinally extending grooves along each of their respective longitudinal edges such that, when paired in abutting relation to form a complete tube, the inserts 238 define inner 240 and outer 242 pairs of coaxial and longitudinally extending channels in inserts 238.

A pair of knife bands 244 are slidably supported within outer channels 242 and extend therethrough. Knife bands 244 are affixed to knife cam 220 at a proximal end and to knife holder 74 at a distal end such that pivoting handles 216 slides knife holder 74 within pusher 62 thereby transmitting the motion through tube 208.

Referring to FIGS. 17a and b retractor portion 206 includes a shortened clamp rod 248 extending into external cup 48 at a proximal end thereof and having the leaf-spring snap-fit type of engagement with center rod assembly 98 referred to above in ring applier 10 and is supplied with a similar trocar tip 104, FIG. 17c.

Furthermore, as shown in FIG. 17d, center rod assembly 98 may be partially hollow and have a transverse vent hole 98a to allow excess gas pressure to escape.

As shown in FIGS. 18a and 18b, in a second embodiment of shortened clamp rod 248, an annular projection 250 on clamp rod 248 engages an annular depression 252 on center rod 98 for a snap-fit type of engagement similar to that of the first embodiment but without a plurality of leaf springs 95. A pair of trocar points 254 and 256 similar to those mentioned above are provided for snap-fit connection to clamp rod 248 and annular depression 252 on center rod 98 respectively.

Referring to FIGS. 17b, 18b and 23, retractor portion 206 further includes a pair of clamp bands 246 slidably suspended within inner channels 240 and attached at distal ends thereof to clamp rod 248. Bands 246 are affixed to cam-clamp 230 at proximal ends thereof such that turning tail member 222 moves cam-clamp 230 and thus center rod assembly 98 thereby transmitting the motions of cam-clamp 230 through tube 208 to center rod assembly 98.

Figure 16:
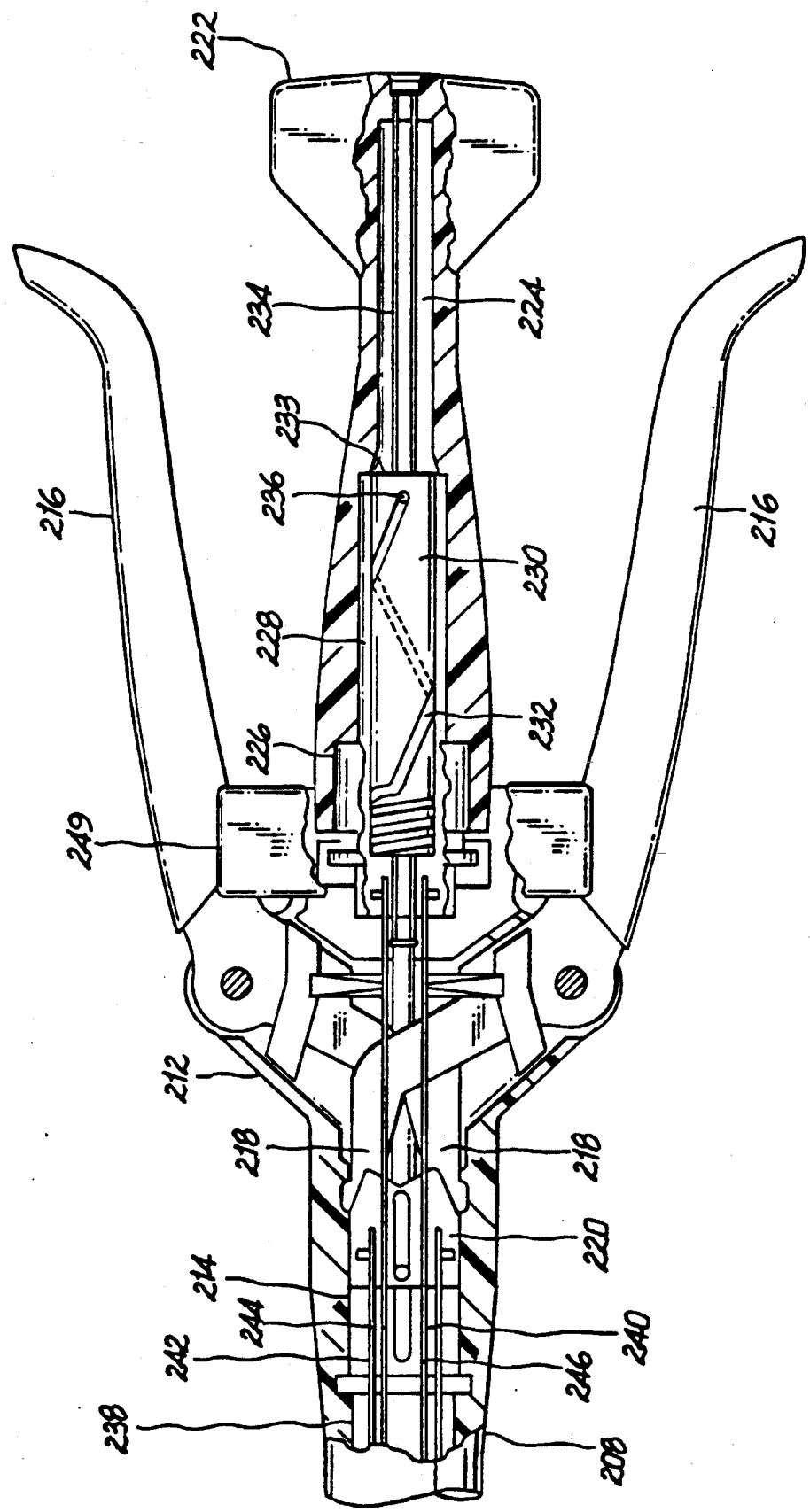
FIG. 16 is a side detail view of the handle portion of the alternative embodiment.
Figure 19A:
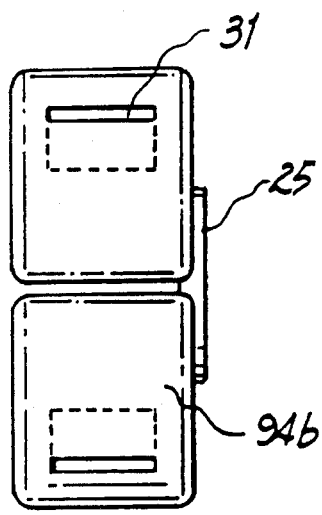
FIG. 19a, 19b, 19c, 19d and 19e are detail views of a female outer ring.
Figure 19B:
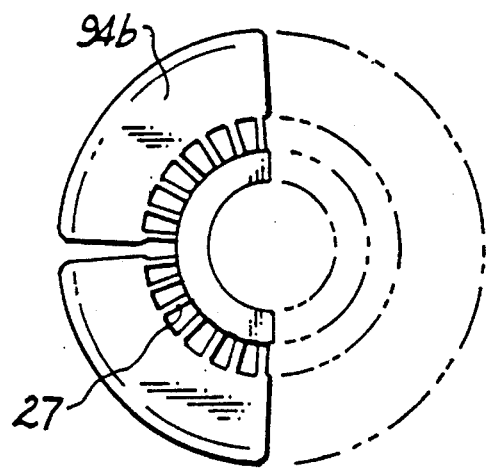
Figure 19C:
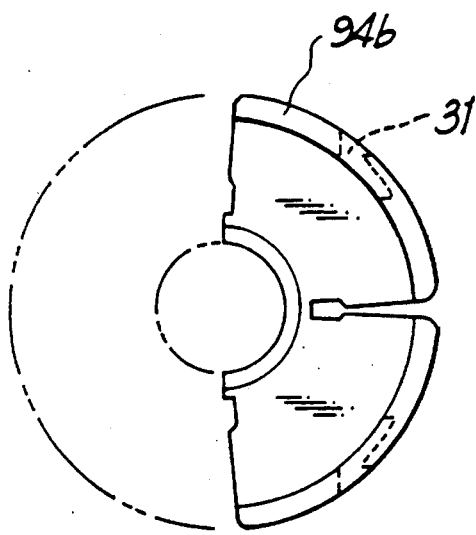
Figure 19D:
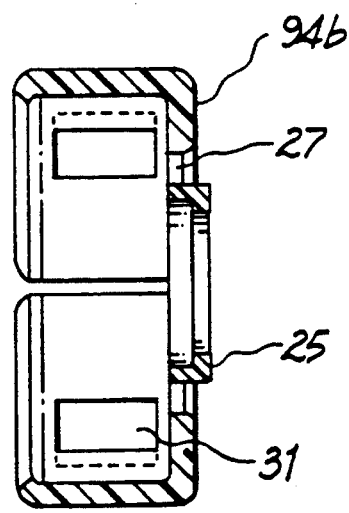
Figure 19E:
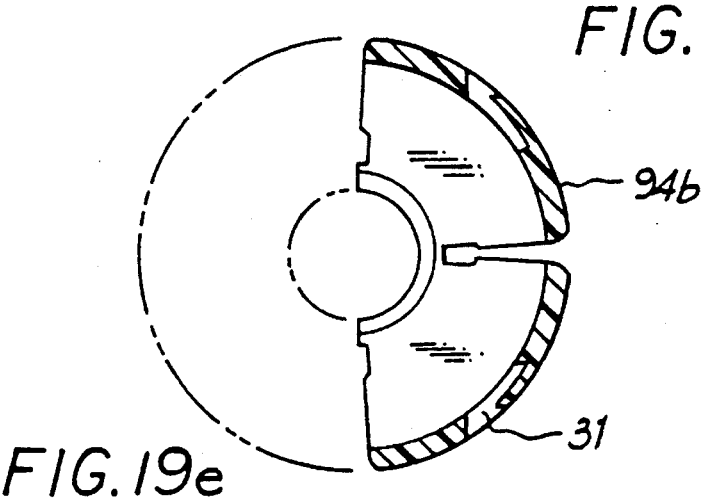
Figure 20A:
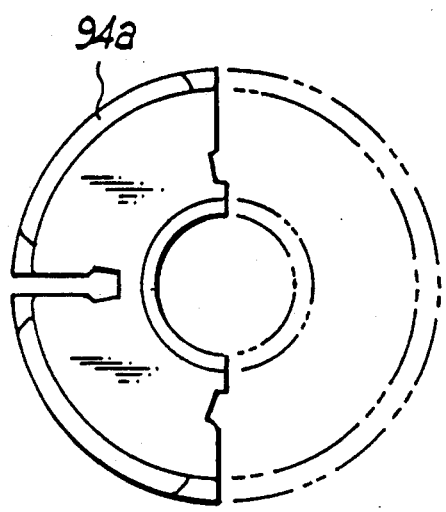
FIGS. 20a, 20b, 20c, 20d and 20e are detail views of a male outer ring.
Figure 20B:
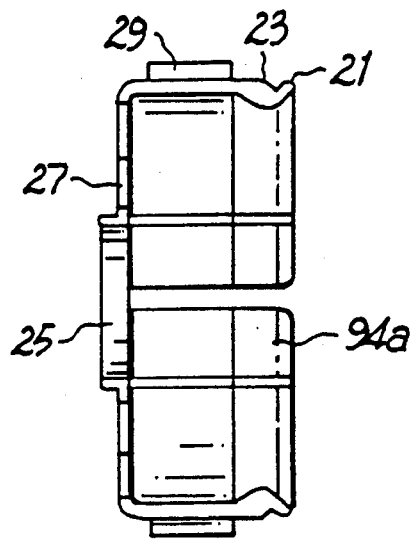
Figure 20C:
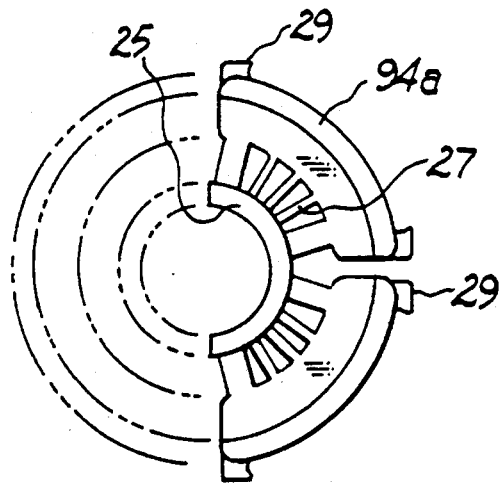
Figure 20D:
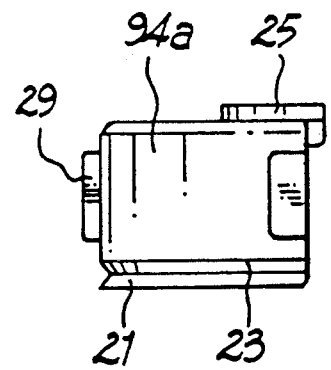
Figure 20E:
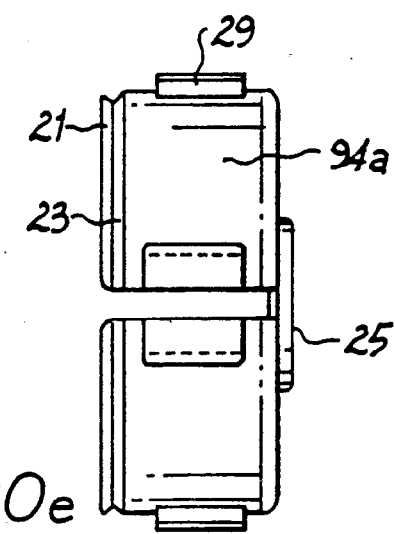

Referring to FIGS. 15, 16, and 23 ring applier 200 is preferably provided with a wing safety 249 rotatably mounted on wing body 212 and positioned between handles 216 such that safety 249 blocks movement of handles 216 in a first position and allows free movement of handles 216 when safety 249 is rotated to a second position.

In use, ring applier 200 is readied and operated in similar fashion to ring applier 10. In one embodiment of ring applier 200, after center rod assembly 98 has been deployed in a distal section of tubular tissue, both trocar tips 254 and 256 are removed from the surgical field by grippers 105 prior to attaching center rod assembly 98 to clamp rod 248 as shown in FIG. 18b.

Turning tail member 222, analogous to the turning of clamp knob 34 above, draws helical cam-clamp 230 rearward initially a rapid rate to provide quick approximation of rings 52 and 94 and subsequently at a slower rate for more precise approximation of rings 52 and 94. Increased torque accompanies the slower approximation rate to apply a higher clamping force between rings 52 and 94 and the tissue section clamped therebetween.

Pivoting handles 216 is analogous to the pivoting of handle 24 above in that the knife holder 74 is forced forward to initially insert locking inner ring 72 into intermediary ring 52, subsequently core the ring assembly and thereafter finally push the multi-ring assembly and clamped tissue free of ring applier 200.

Figure 24:
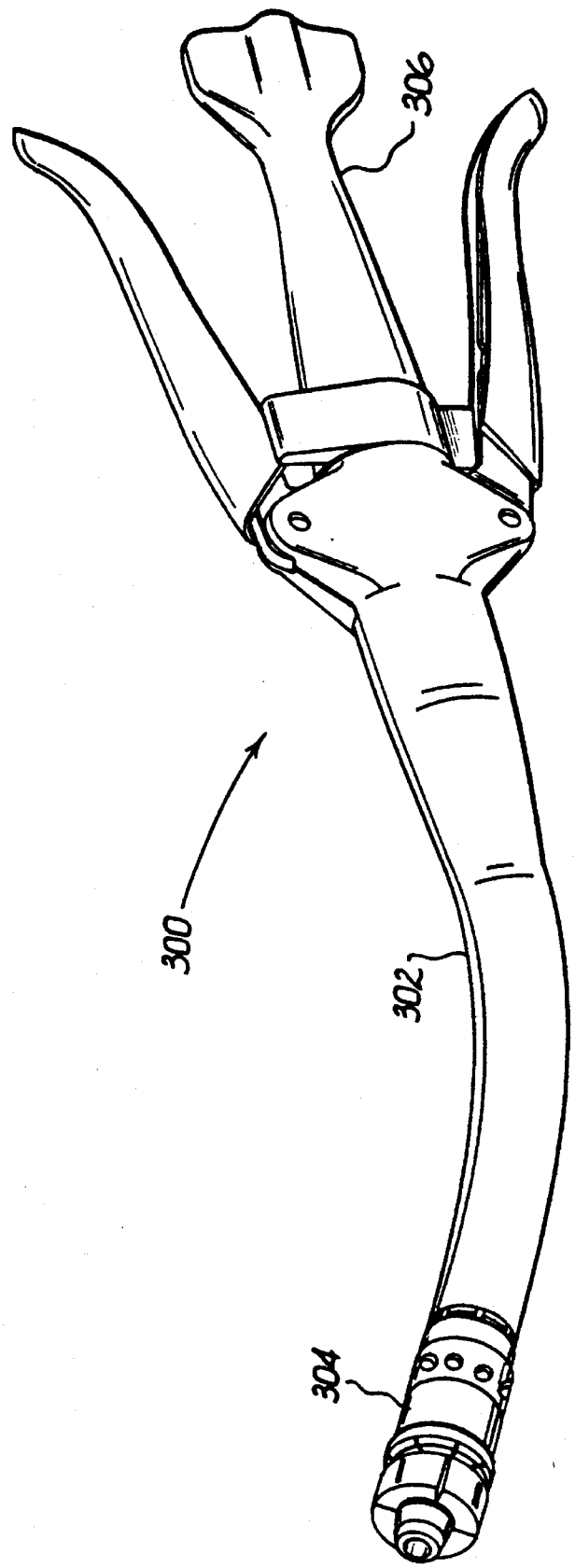
FIG. 24 is a perspective view of another embodiment of the invention.

Another embodiment of the present invention is best illustrated in FIG. 24 wherein ring applier 300 generally includes a body portion 302, a head portion 304 and a retractor portion 306 extending through body portion 302 and head portion 304.

Figure 25:
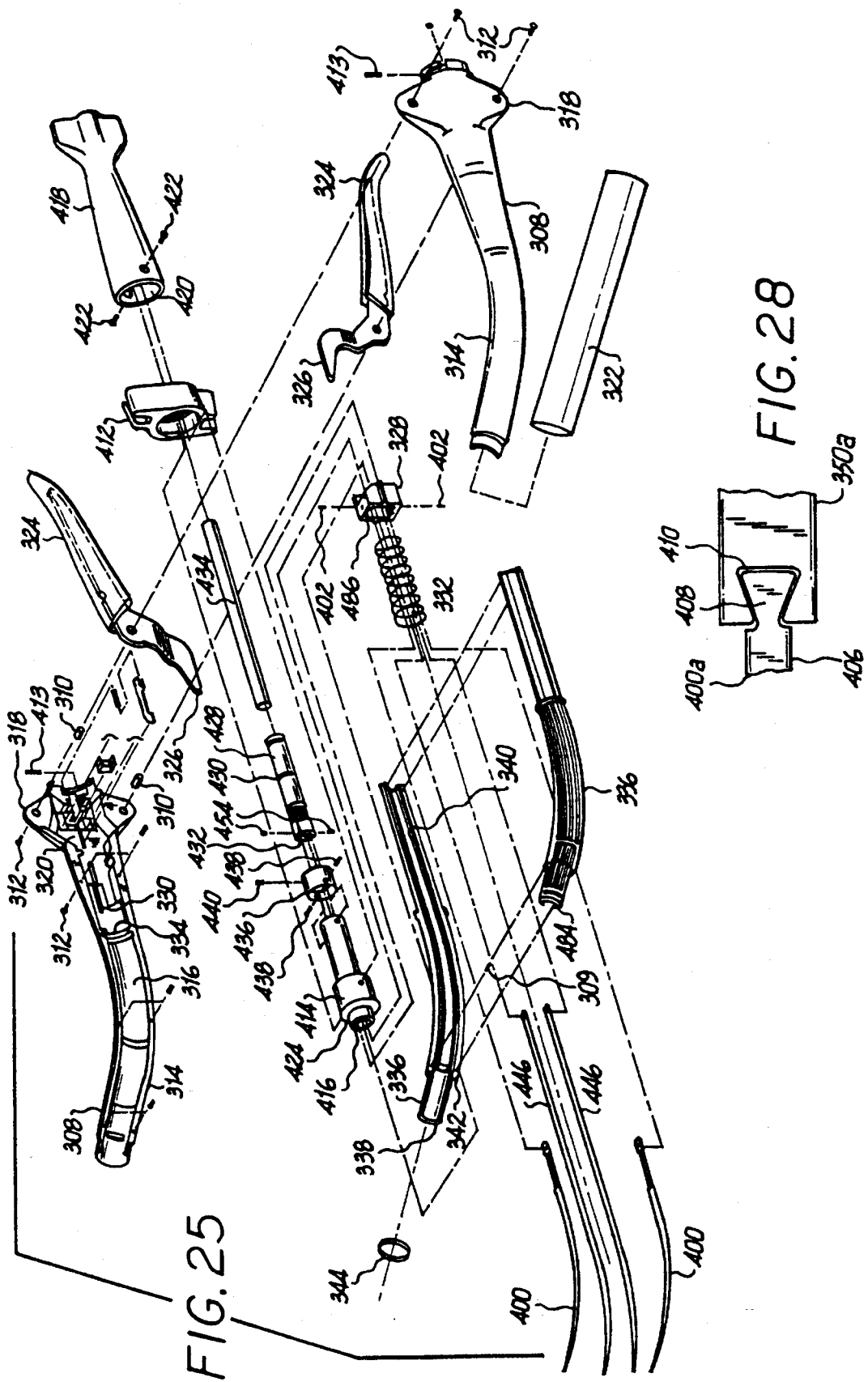
FIG. 25 is an exploded perspective view of the body portion and retractor portion thereof.

As shown in FIG. 25, body portion 302 is comprised of a pair of body halves 308 which, when combined by alignment pins 309, and fastened together by means of bushing inserts 310 and screws 312, form an elongated front end tube 314, preferably curved, having a cavity 316 therein. Body halves 308 have wing shaped back ends 318 which, when combined, form a cavity 320 communicable with cavity 316. A shrink wrap 322 may be provided to aid in holding body halves 308 together and present a smooth outer surface when ring applier 300 is assembled. Body portion 302 further includes a pair of handles 324, pivotally and opposingly mounted on bushing insert 310, each handle 324 having an inwardly directed front end 326 extending through cavity 320 and into cavity 316. A knife cam 328 is slidingly disposed within cavity 316 on side grooves 330 formed within body halves 308 and is in abutting contact with inwardly extending front ends 326 of handles 324 such that pivoting handles 324 together forces knife cam 328 forward within cavity 316. A knife retractor spring 332 is located within body portion 302, and positioned between flange 334 on body halves 308 and knife cam 328, to bias knife cam 328 rearwardly.

A pair of semicircular guide inserts 336 are disposed within tube cavity 316 and extend therethrough. Each insert 336 has a pair of longitudinally extending projections 338 along each of their respective longitudinal edges such that, when paired in abutting relation to form a complete tube, and positioned within mating body halves 308, define inner 340 and outer 342 pairs of coaxial and longitudinally extending channels, similar to channels 240 and 242 described hereinabove with respect to ring applier 200, in inserts 336.

Figure 26:
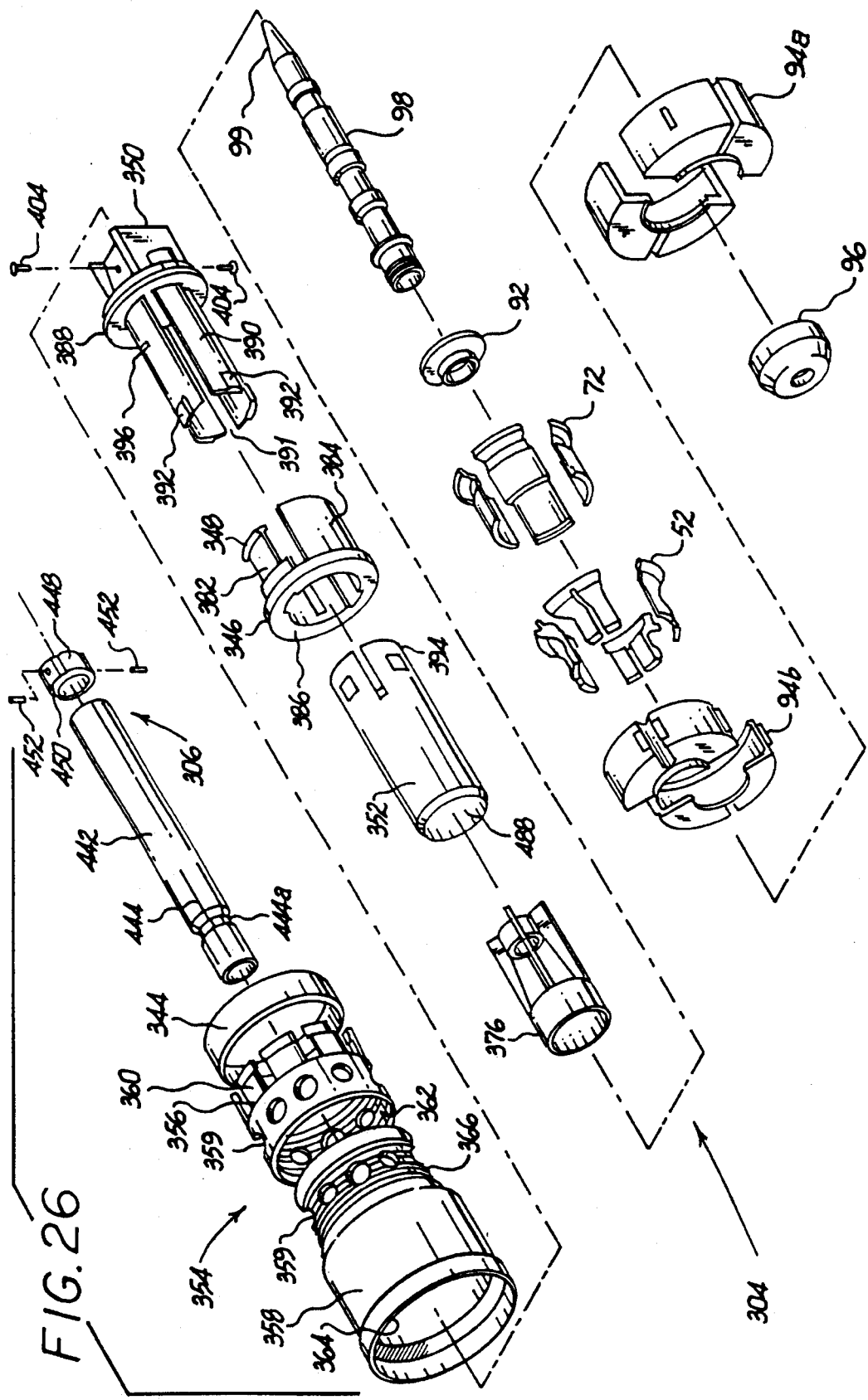
FIG. 26 is an exploded perspective view of the head portion of FIG. 24.
Figure 27:
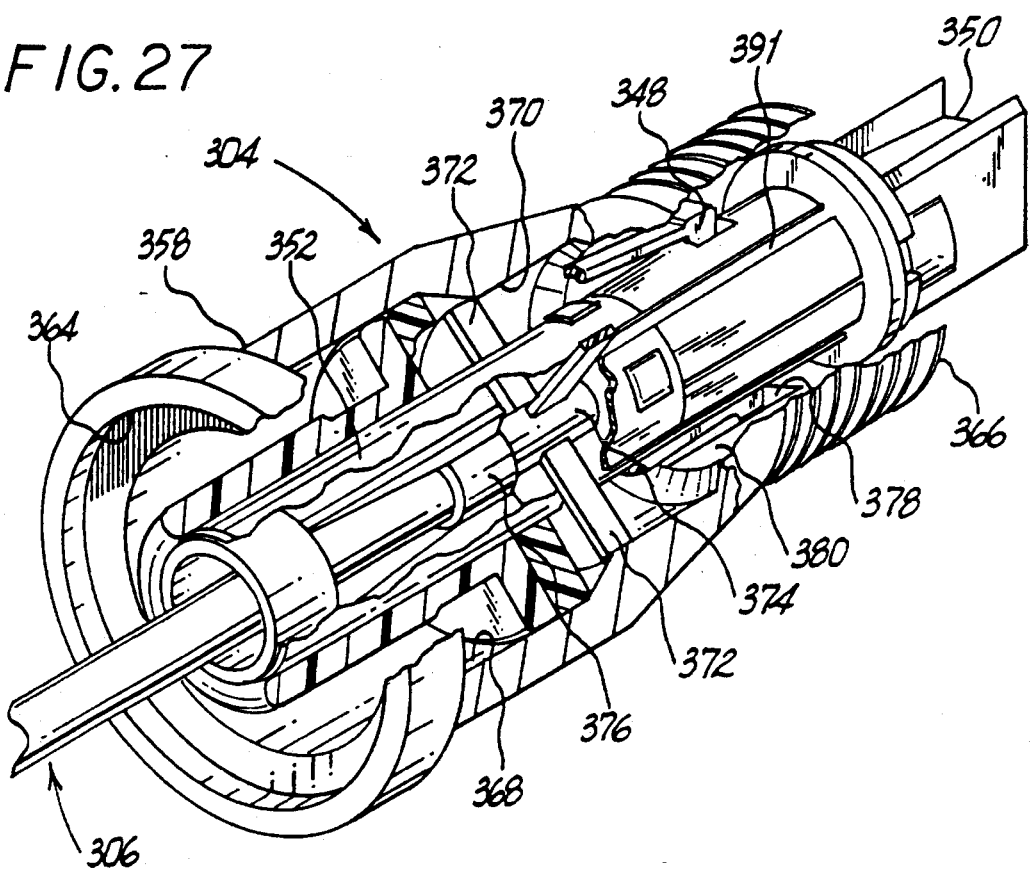
FIG. 27 is a perspective view, partially shown in section, of the head portion.

Referring to FIGS. 26 and 27 head portion 304 is similar to head portion 14 referred to above and contains similar parts/elements recited therein including pusher 346 having integral shifter keys 348, knife holder 350 and knife blade 352 which function together in the same manner recited hereinabove. Specifically, referring now to FIG. 26 head portion 304 comprises an external cup 354 having a rear portion 356 and a front portion 358. Rear portion 356 includes a plurality of flexible fingers 360 at a proximal end and a threaded interior 362. A support ring 344 (FIG. 25) is provided to hold fingers 360 against body halves 308 thereby securing rear portion 356 to body halves 308.

Front portion 358 has a grooved distal end 364 for support of intermediary ring 52 and is threadably engagable with rear portion 356 of external cup 354 thereof by means of threaded surface 366. As best seen in FIG. 27, front portion 358 forms an enlarged bore area 368 at a distal end and a reduced area portion 370 at a proximal end beneath threaded surface 366. Front portion 358 has a plurality of crosswise support members 372 extending inwardly within enlarged bore area 368. Support members 372 meet within enlarged bore area 368 at a center boss 374 which surrounds a centerline of ring applier 300 to maintain an unobstructed bore therethrough and for support of a knife shield 376 as described hereinbelow.

Front portion 358 of external cup 354 further includes a plurality of dwell recesses 378 located on an inner surface 380 (FIG. 27) of front portion 358 and disposed within a threaded section 366 of front portion 358 to guide shifter keys 348.

Figure 31:
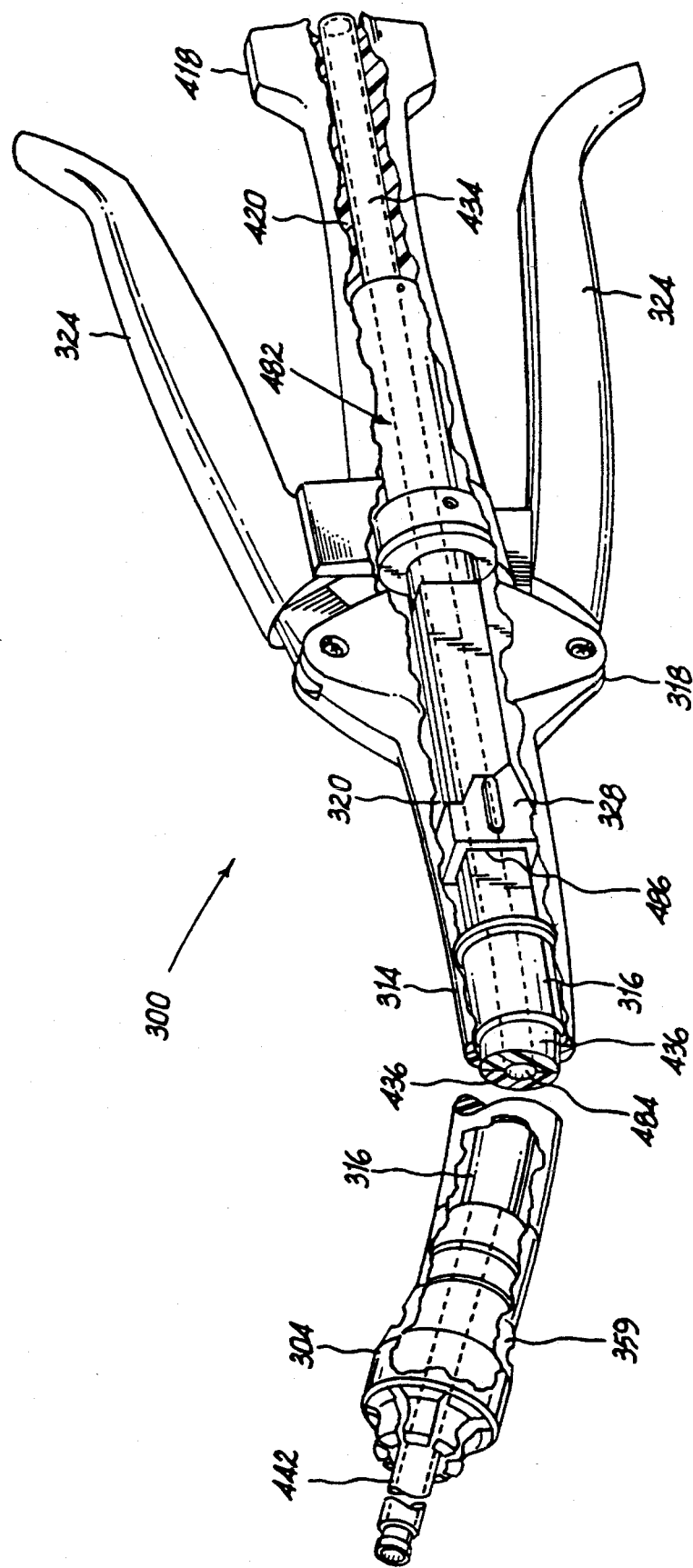
FIG. 31 is a perspective view, partially shown in section, of the instrument of FIG. 24, illustrating the throughbore.
Figure 32:
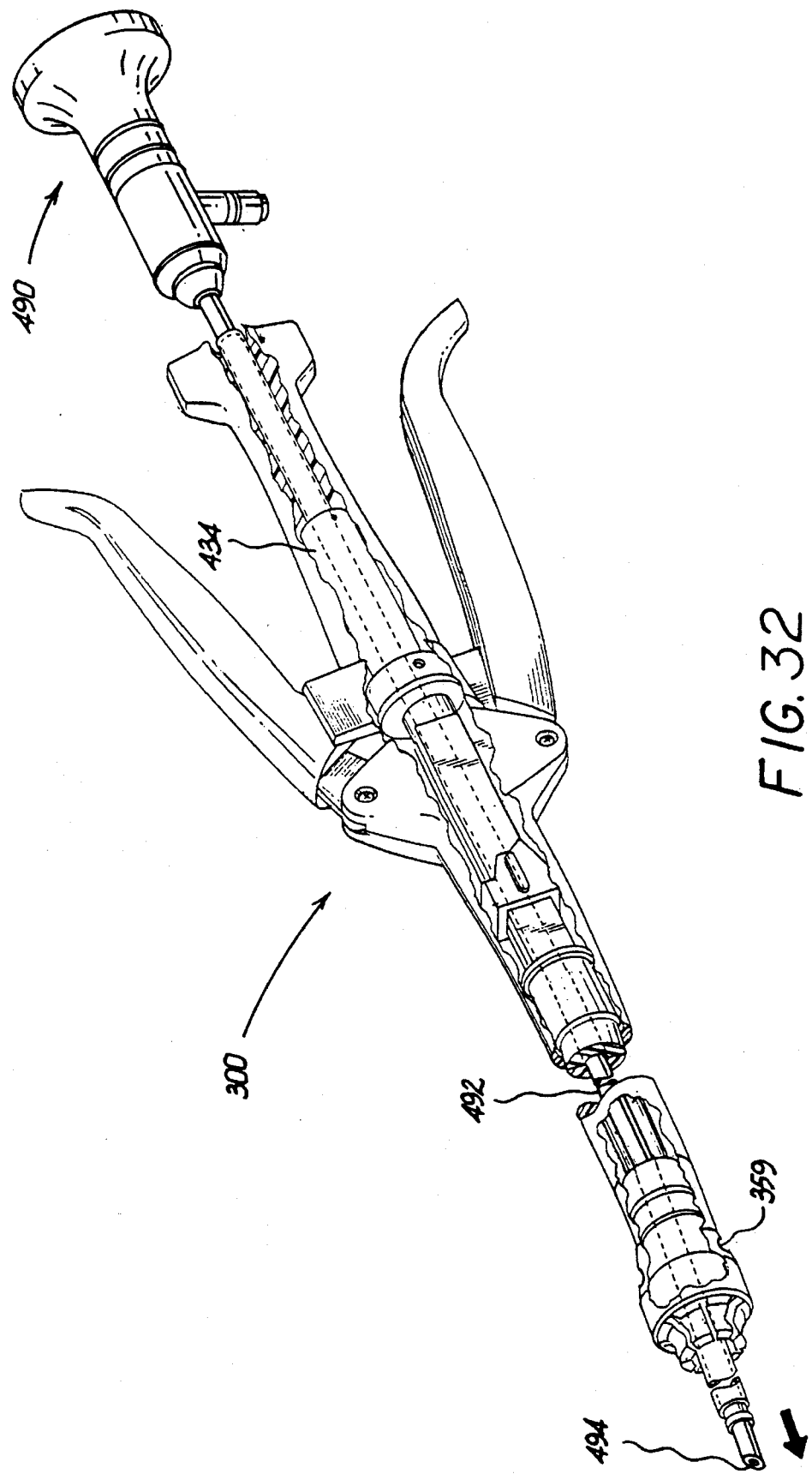
FIG. 32 is a perspective view, partially shown in section, of the instrument of FIG. 31, with an accessory instrument inserted therethrough.

Additionally, front portion 358 and rear portion 356 may be provided with venting means similar to that described in U.S. Pat. No. 4,304,236 to Conta et al. the disclosure of which is incorporated by reference hereinabove, including vent holes 359 (FIGS. 26, 31 and 32).

Pusher 346 (FIG. 26), having resilient means in the form of a pair of flexible arms 382 which terminate in integral shifter keys 348 and having a pair of relatively rigid driving arms 384, is slidably disposed within external cup 354. Pusher 346 further has a circumferential flange 386 at a distal end which resides in enlarged bore area 368 of external cup 354. The longitudinal openings between arms 382 and driving arms 384 facilitate sliding pusher 346 around crosswise support members 372. Pusher 346 slidably supports inner ring 72 within enlarged bore area 368 of external cup 354.

Knife holder 350 has a circumferential flange 388 at a proximal end and is slidably disposed within pusher 346. Knife holder 350 further includes a plurality of support arms 390 having outwardly projecting tabs 392 for engagement with flexible end portions 394 of circular knife blade 352 to affix knife blade 352 to a distal end of knife holder 350. Engagement means in the form of shifter key recesses 396 are formed on an outer surface of two opposing support arms 390. A plurality of longitudinal channels 391 between arms 390 slidably surround support members 372, respectively, and when combined with knife blade 352 serve to limit the travel of the assembled knife blade 352 and holder 350 within external cup 354. Finally knife shield 376 is disposed within knife blade 352 and frictionally engages central boss 374. Knife shield 376 projects past knife blade 352, when knife blade 352 is in a proximalmost position, to protect the user.

The motion of handles 324 is transmitted to knife holder 350 by means of a pair of knife bands 400 (FIG. 25) which are slidably supported within outer channels 342 and extend therethrough. Knife bands 400 are affixed to knife cam 328 at a proximal end by means of pins 402 and to knife holder 350 at a distal end by means of pins 404 such that pivoting handles 324 slides knife holder 350 within pusher 346 thereby transmitting the motion of handles 324 through inserts 336 in front end cavity 316.

In an alternate embodiment, knife bands 400a are substituted for knife bands 400 and knife holder 350a is substituted for knife holder 350. Ends 406 of knife bands 400a are affixed to knife holder 350a and knife cam 328 by means of flared projections 408 on ends 406 of bands 400 and corresponding notches 410 on knife holder 350a and knife cam 328 as shown in FIG. 28. This arrangement eliminates the need for pins 402 and 404 and facilitates maintaining an open channel throughout ring applier 300.

Figure 30:
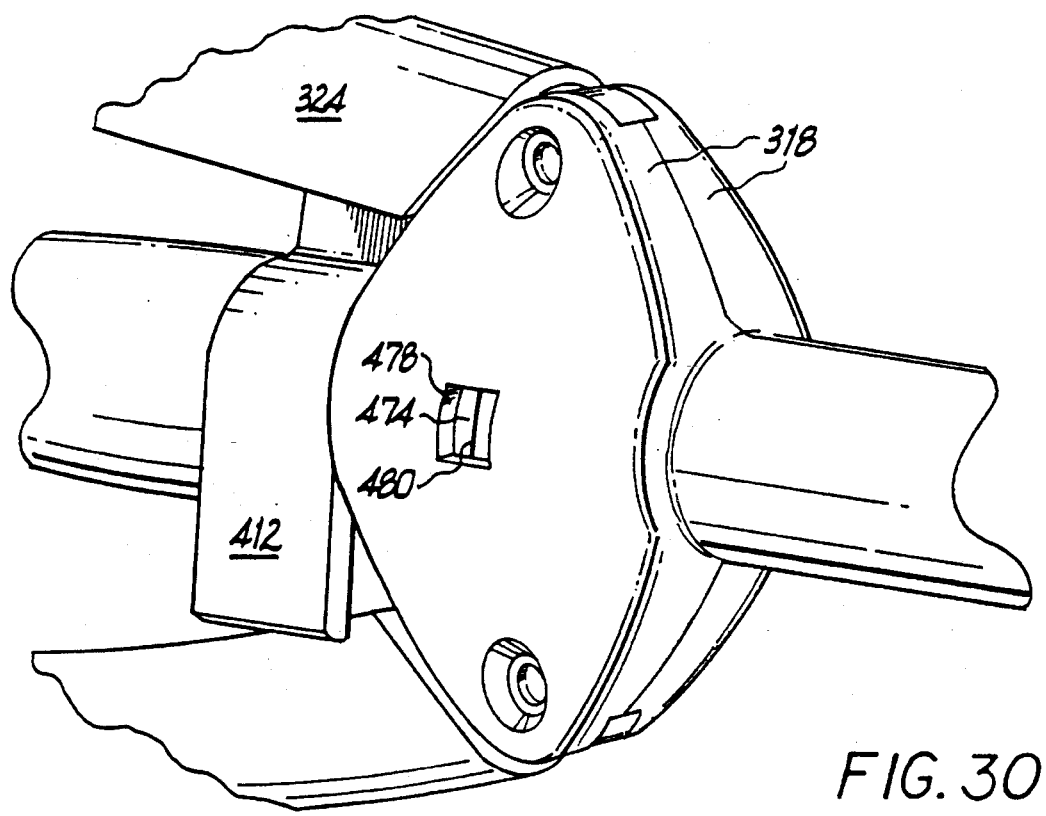
FIG. 30 is a partial side perspective view of the body portion.

Referring to FIGS. 25, 29 and 30, ring applier 300 is preferably provided with a wing safety 412 rotatably mounted on wing shaped back ends 318 and positioned between handles 324 such that safety 412 blocks movement of handles 324 in a first position and allows free movement of handles 324 when safety 412 is rotated to a second position. Springs 413 are provided between wing safety 412 and wing shaped back end to bias wing safety 412 into the first or locked position.

At a proximal end of ring applier 300, as shown in FIG. 25, retractor portion 306 includes a barrel 414, defining a bore 416, and rotatably attached to wing shaped back end 318 at a distal end, which extends backwards from wing shaped back end 318 and is centered between opposing handles 324. A tail member 418, defining a bore 420 communicable with wing cavity 320 is rigidly affixed to barrel 414 by means of screws 422 at a distal end of barrel 414 for rotatable support of tail member 418 on wing shaped back end 318. Flange 424 on barrel 414 rotates within grooves 426 (FIG. 29) on body halves 308.

A cam-clamp 428 (FIG. 25) having a variable helical depression 430 on an outer surface thereof, and defining a bore 432 is slidingly suspended within barrel bore 416 by means of a guide tube 434 which is affixed to wing shaped back end 318 at a first end and extends through bore 432 in cam-clamp 428 to guide cam-clamp 428 within barrel bore 416. Variable helical depression 430 in cam-clamp 428 is initially of a slow rate of twist at a proximal end of cam-clamp 428 to provide a rapid initial approximation of rings 52 and 94. At the distal end of cam-clamp 428 the helical depression 430 changes to a rapid rate of twist to provide slower more precise approximation of rings 52 and 94 and to provide increased torque for clamping rings 52 and 94 around ends of tubular tissue sections.

A barrel insert 436 is attached to a proximal end of barrel 414 by means of pins 438. A guide pin 440 is rigidly affixed to barrel insert 436 at a proximal end thereof such that a free end of pin 440 extends into and engages helical depression 430 of cam-clamp 428. By rotating tail member 418, barrel 414 drives pin 440 in helical depression 430, thereby drawing cam-clamp 428 rearwardly along guide tube 434 initially at a fast rate and subsequently in a slower, stronger and more precise fashion.

Referring again to FIGS. 26 and 27, retractor portion 306 further includes a shortened clamp rod 442 extending into external cup 354 at a proximal end thereof and having slots 444 to allow the tube neck 444a to expand to create a snap-fit type of engagement with a center rod assembly 98 similar to that referred to above in ring applier 10 and is supplied with a similar trocar tip 99.

As shown in FIG. 25, retractor portion 306 further includes a pair of clamp bands 446 slidably suspended within inner channels 340 and attached at distal ends thereof to clamp rod end 448 (FIG. 26) by insertion of band 446 into slots 450 of clamp rod end 448 and affixed thereto by means of pins 452. Bands 446 are affixed to cam-clamp 428 at proximal ends thereof by means of pins 454. Clamp rod end 448 is affixed around clamp rod 442 to connect clamp bands 446 thereto. Turning tail member 418 moves cam-clamp 428, and thus center rod assembly 98, axially thereby transmitting the motions of cam-clamp 428 through channels 340 to center rod assembly 98. Alternatively, clamp bands 446 may be connected to clamp rod end 448 and cam-clamp 428 by means of the flared projections/notches system described with respect to knife bands 400 hereinabove.

A particularly advantageous feature of ring applier 300, as shown in FIGS. 29 and 30, is lockout means in the form of a lockout safety 456 which prevents turning wing safety 412 unless and until clamp band 446 is fully retracted. Lockout safety 456 includes a lock plate 458 slidably supported within plate channel 460 formed in wing shaped back end 318. Lock plate 458 includes a centrally positioned dog leg shaped engagement leg 462 and a lock tab 464 at a proximal end for engagement with a metal insert 470, which is located in notched area portion 472 of wing safety 412. Projection 466 is provided at a proximal end of one clamp band 446 to contact and move engagement leg 462. A lock spring 468 is provided to bias lock plate 458 distally in a locked position. Also included is a display slide 474 and leaf springs 476 disposed between lock plate 458 and wing shaped back end 318 such that slide 474 is visible through window 478 in wing shaped back end 318. An indicator mark 480 on display slide 474 shows through window 478 and indicates when clamp band 446 is fully retracted and ring applier 300 is ready to fire.

In a preferred embodiment of ring applier 300, a longitudinal through bore 482 (FIG. 31) extends throughout the length of ring applier 300 to allow accessory instruments such as endoscopes, grasping or cutting forceps, and the like to be inserted into ring applier 300 at a proximal end and be communicable with a distal end of ring applier 300. As best illustrated in FIGS. 31 and 32, throughbore 482 extends through guide tube 434 positioned within tail bore 420 in tail member 418. As noted above, guide tube 434 is affixed to wing shaped back end 318 and extends into wing cavity 320. A channel 484 is formed by paired guide inserts 436, within tube cavity 316 in front end tube 314. Bore 482 continues from wing cavity 420 through channel 484 which is communicable with wing cavity 420.

In this embodiment it can be readily appreciated that to maintain an unobstructed bore 482 throughout ring applier 300, knife cam 328 must contain a cavity 486 as shown in FIGS. 25 and 31, to allow a continuous communicable passageway through wing cavity 320. Additionally, inwardly directed ends 326 (FIG. 25) of pivotable handles 324 should allow enough clearance around bore 482 so as not to obstruct bore 482.

As shown in FIG. 25, paired inserts 336, and thus channel 484, terminate within cavity 316 proximally of head portion 304. Therefore, bore 482 extends on through tube cavity and is coaxial therewith. In the preferred embodiment, knife holder 350 is hollow having a knife bore 488 (FIG. 26) coaxial and communicable with tube cavity 316. Thus bore 482 continues from channel 484 through tube cavity 316 and on through knife holder 350. Finally, bore 482 extends through and exits out a distal end of clamp rod 442 which is also communicable and coaxial with tube cavity 316.

Preferably, bore 482 is of circular cross section having a minimum inner diameter on the order of approximately 2 to 6 millimeters and more preferably approximately 5 millimeters.

An endoscope 490 may be inserted through bore 482, as best shown in FIG. 32. Typically endoscope 490 includes a barrel section 492 which extends through bore 482 and terminates in a lens 494 located at a distal end of barrel section 492.

While the provision of a relatively rigid endoscope has been illustrated with respect to the straight bodied ring applier of FIG. 32, it is within the contemplated scope of the invention to provide curved bodied ring applier 300 with a relatively flexible endoscope for use therein. And while the provision of a longitudinally extending bore has been described with regard to the present ring applier, it is within the contemplated scope of the invention to provide other surgical instruments with a bore therethrough to provide auxiliary access to the operative site for accessory instruments, such as, for example, endoscopes, graspers, cutters and the like.

In use, ring applier 300 is readied and operated in similar fashion to ring applier 10 as shown in FIGS. 9–13. In one embodiment of ring applier 300, after center rod assembly 98 has been deployed in a distal section of tubular or hollow organ tissue, trocar tip 104 is removed from the surgical field by grippers (FIG. 11) prior to attaching center rod assembly 98 to clamp rod similar to that shown in FIG. 18b hereinabove.

After ring applier 300 has been inserted into a patient an endoscope may be inserted through bore 482, as best shown in FIG. 25. Endoscope 490 may be used to locate and view the areas of tissue to be joined. Additionally, gripping or cutting devices may be inserted through bore 482 to grasp or cut sutures or tissue or the like at the operative site before or after anastomosis.

Turning tail member 418, analogous to the turning of clamp knob 34 above, draws cam-clamp 428 rearward initially a rapid rate to provide quick approximation of rings 52 and 94 and subsequently at a slower rate for more precise approximation of rings 52 and 94. Increased torque accompanies the slower approximation rate to apply a higher clamping force between rings 52 and 94 and the tissue section clamped therebetween.

In the embodiments with the lockout safety 456, lock tab 464 is initially biased by spring 468 into engagement with metal insert 470 thereby locking wing safety 412 from rotation. When clamp band 446 is fully drawn rearwardly, projection 466 abuts engagement leg 462 moving lock plate 458, and thus lock tab 464, proximally out of engagement with metal insert 470 and into notched area portion 472 of wing safety 412 allowing wing safety 412 to turn freely. Indicator mark 480 shows through window 478 indicating that cam-clamp 428 is fully retracted and that wing safety 412 is free to rotate thereby unblocking handles 324.

The pivoting of handles 324 is analogous to the pivoting of handles 24 above in that the knife holder 350 is forced forward carrying with it pusher 346 to initially insert locking inner ring 72 into intermediary ring 52.

Figure 33:
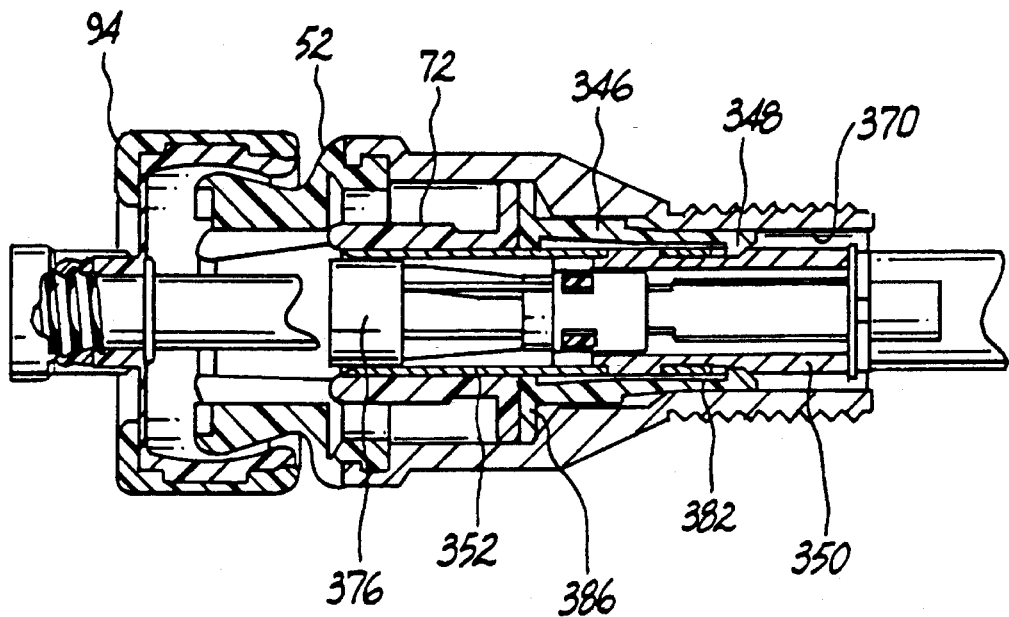
FIG. 33 is an enlarged side cross-sectional detail view of the head portion of the embodiment of the FIG. 24 showing an outer ring retracted over an intermediary ring.

However, in the aforementioned embodiments, the shifter keys moved within shifter key channels located within the pusher. In ring applier 300, shifter keys 348, being integral with flexible arms 382 of pusher 346, are biased into engagement with shifter key recesses 396 in knife holder 350 when in reduced area portion 370 (FIG. 33). Thus pusher 346 moves with knife holder 350 as handles 324 are pivoted to insert inner ring 72 into intermediary ring 52.

Figure 34:
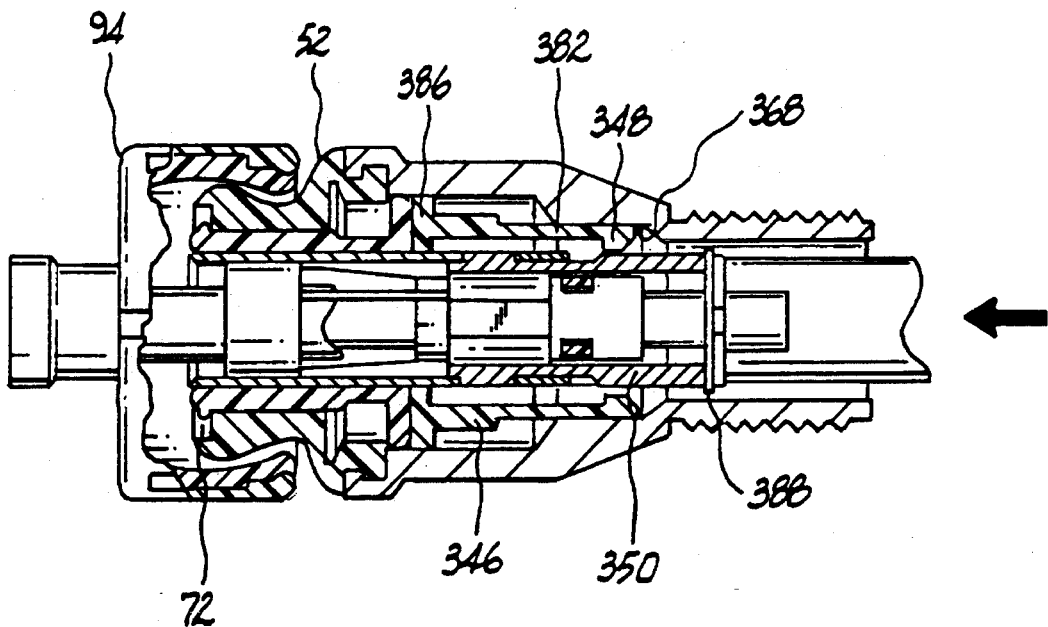
FIG. 34 is a view similar to FIG. 33 showing insertion of an inner locking ring.
Figure 35:
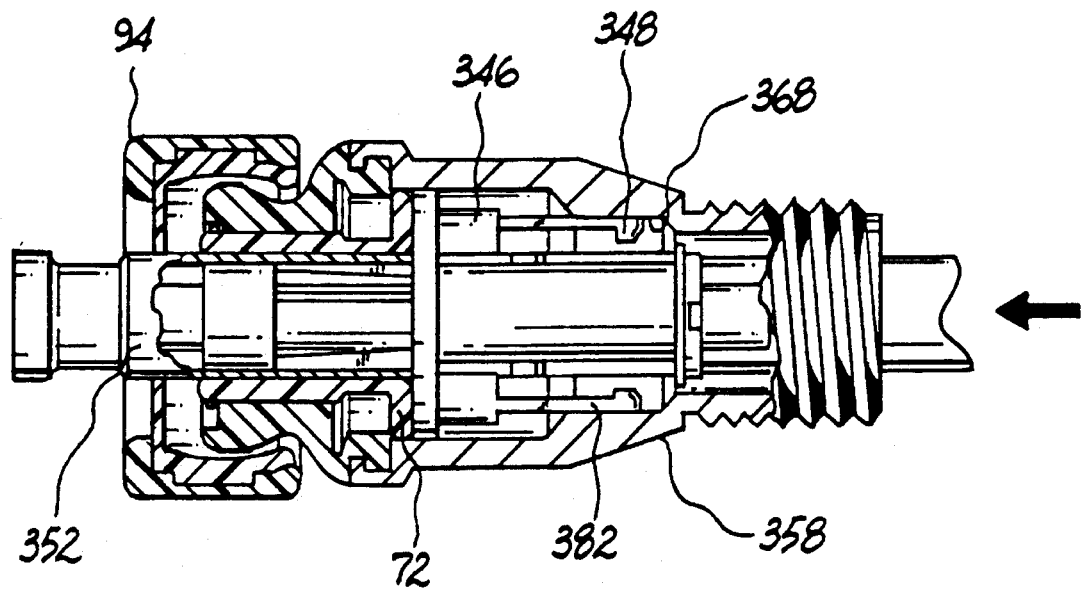
FIG. 35 is a view similar to FIG. 34 showing advancement of the coring means through the outer ring.
Figure 36:
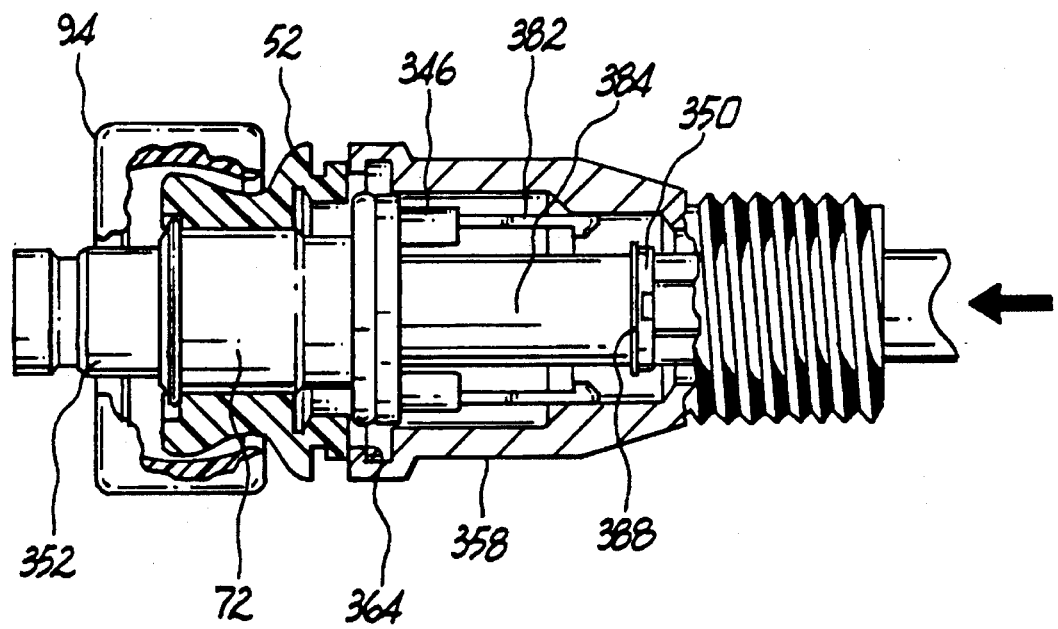
FIG. 36 is a view similar to FIG. 35 showing the release of the assembled ring assembly from the frame.

When inner ring 72 is fully inserted, shifter keys 348 flex outwardly (FIG. 34) into enlarged area portion 368 of external cup 354 and out of shifter key recesses 396. Disengaging pusher 346 from knife holder 350 allows knife blade 352 to advance independently of pusher 346 to core the centers of rings 94 (FIG. 35) and tissue clamped therebetween in a manner similar to that described hereinabove. Thus shifter keys 348 serve to alternately engage and disengage pusher 346 from knife holder 350 and thus preventing release of the assembled rings prior to completion of coring of the excess tissue. After coring, flange 388 on knife holder 350 abuts driving arms 384 of pusher 346 to finally push assembled rings free from grooved distal end 364 of front portion 358 and thus from ring applier 300 (FIG. 36).

As noted above, support members 372 (FIG. 27) serve to limit the travel of knife and pusher 346. After handles 324 are released, spring 332 biases knife cam 328 proximally thereby drawing knife blade 352 proximally. Knife shield 376 projects past a distal end of knife blade 352 when knife blade 352 is in the proximalmost position to protect the user.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A surgical instrument for application of surgical fasteners to a first hollow organ tissue section and a second hollow organ tissue section for anastomosis thereof, said surgical instrument comprising:
    a) a frame portion;
    b) retraction means slidingly disposed within said frame portion for collecting a first tissue section and a second tissue section to be fastened, said frame portion and said retraction means co-defining a bore extending axially throughout the length of the instrument and sized to receive accessory instruments therethrough;
    c) pushing means slidingly disposed within said frame portion for application of at least a first and a second monolithic interlocking surgical fastener to the collected first and second tissue sections;
    d) coring means slidingly disposed within said frame portion, and engagable with said pushing means for advancement of said pushing means, for coring excess tissue captured between the collected first and second tissue sections; and
    e) resilient means associated with said pushing means for alternately engaging and disengaging said pushing means with said coring means, wherein said resilient means engages said pushing means with said coring means during application of the first and second surgical fasteners and said resilient means disengages said pushing means from said coring means during coring.

2. The surgical instrument as recited in claim 1 wherein said coring means includes a knife assembly, having a blade member at a distalmost end for cutting said excess tissue, said knife assembly having engagement means for engaging said resilient means.

3. The surgical instrument as recited in claim 2 further comprising a knife shield affixed to said frame portion and extending distally of said blade member when said blade member is in a proximalmost position.

4. The surgical instrument as recited in claim 2 further comprising a spring member for biasing said blade member in a proximalmost position.

5. The surgical instrument as recited in claim 1 further comprising lockout means associated with said frame portion for blocking movement of said coring means until the first tissue section and the second tissue section are substantially collected by said retraction means.

6. The surgical instrument as recited in claim 1 further comprising venting means to allow escape of excess air pressure between the collected first and second tissue sections and from within the instrument.

7. A surgical instrument for application of surgical fasteners to a first and a second hollow organ tissue section, said surgical instrument comprising:
    a) a frame portion defining a bore extending axially throughout the length of said frame portion and adapted for receipt of accessory instruments therethrough;
    b) retracting means slidingly disposed within said frame portion for approximation of a first tissue section and a second tissue section, said retracting means movable between a first position wherein the first and the second tissue sections are substantially spaced apart to a second position wherein the first and the second tissue section are substantially approximated;
    c) pushing means slidingly disposed within said frame portion for applying at least a first and a second monolithic interlocking surgical fastener to the approximated first and second tissue sections to fasten the first tissue section to the second tissue section;
    d) coring means slidingly disposed within said frame portion, and engagable with said pushing means for advancement of said pushing means, for coring excess tissue captured between the fastened first and second tissue sections;
    e) resilient means associated with said pushing means for alternately engaging and disengaging said pushing means with said coring means; and
    f) lockout means associated with said frame portion for blocking activation of said pushing means and said coring means until the first and the second tissue sections have been substantially approximated by said retraction means.

8. The surgical instrument as recited in claim 7 further comprising a handle mechanism operatively associated with said frame portion, said lockout means blocking said handle mechanism to prevent activation of said pushing means and said coring means until the first and second tissue sections have been substantially approximated.

9. A surgical instrument for application of surgical fasteners to a first hollow organ tissue section and a second hollow organ tissue section for anastomosis thereof, said surgical instrument comprising:
    a) a frame portion;
    b) retraction means slidably disposed within said frame portion for collecting a first hollow organ tissue section and a second hollow organ tissue section to be fastened;
    c) support means located distally of said frame portion for holding at least one surgical fastener;
    d) a tail member rotatably mounted in axial alignment with said frame portion;
    e) a handle having a distal end and a proximal end, said handle attached to said frame portion for moving said proximal end of said handle towards said frame portion such that said at least one surgical fastener functionally connects the first and second hollow organ tissue sections; and f) said frame portion, said tail member and said retraction means co-define a bore extending axially through the length of the instrument and sized to receive accessory instruments therethrough.

10. A surgical instrument for application of surgical fasteners to a first hollow organ tissue section and a second hollow organ tissue section for anastomosis thereof, said surgical instrument comprising:

a) a frame portion;

b) retraction means slidingly disposed within said frame portion for collecting a first tissue section and a second tissue section to be fastened, said frame portion and said retraction means co-defining a bore extending axially therethrough and sized to receive accessory instruments therethrough;

c) pushing means slidingly disposed within said frame portion for application of surgical fasteners to the collected first and second tissue sections;

d) coring means slidingly disposed within said frame portion, and engagable with said pushing means for advancement of said pushing means, for coring excess tissue captured between the collected first and second tissue sections; and e) resilient means associated with said pushing means for alternately engaging and disengaging said pushing means with said coring means, wherein said resilient means engages said pushing means with said coring means during application of the surgical fasteners and said resilient means disengages said pushing means from said coring means during coring.

* * * * *